(12) United States Patent
Shimada

(10) Patent No.: US 6,613,574 B2
(45) Date of Patent: Sep. 2, 2003

(54) METHOD TO IDENTIFY INTERFACE RESIDUE IN BIOMOLECULAR COMPLEX

(75) Inventor: Ichio Shimada, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 9 days.

(21) Appl. No.: 09/794,329

(22) Filed: Feb. 28, 2001

(65) Prior Publication Data

US 2002/0055105 A1 May 9, 2002

(30) Foreign Application Priority Data

Jul. 14, 2000 (JP) ........................................ 2000-214997

(51) Int. Cl.[7] ............................................... G01N 33/00
(52) U.S. Cl. ........................... 436/86; 436/173; 436/828
(58) Field of Search ............................. 436/86–88, 173, 436/828

(56) References Cited

PUBLICATIONS

Ramos et al. "Mapping the Interfaces of Protein–Nucleic Acid Complexes Using Cross–Saturation", J. Am. Chem. Soc., 2000, v. 122, pp. 11311–11314.*
Lane et al. "Determining Binding Sites in Protein–Nucleic Acid Complexes by Cross–Saturation", J. Biomol. NMR, 2001, v. 21, pp. 127–139.*
Zuiderweg, "Mapping Protein–Protein Interactions in Solution by NMR Spectroscopy", Biochemistry, Jan. 8, 2002, v. 41, No. 1, pp. 1–7.*
Jayalakshmi e al. "Complete Relaxation and Conformational Exchange . . . ", J. Magn. Reson., 2002, v. 155, pp. 106–118.*
Takashi Yabuki, et al., Dual amino acid–selective and site–directed stable–isotope labeling of the human c–Ha–Ras protein by cell free synthesis, Journal of Biomolecular NMR, vol. 11, 1998, pp. 295–306.

Chojiro Kojima, et al., Solid–Phase Synthesis of Selectively Labeled DNA: Applications for Multidimensional Nuclear Magnetic Resonance Spectroscopy, Methods in Enzymology, vol. 338, 2001, pp. 261–283.

Deisenhofer, J. (1981), Crystallographic refinement and atomic models of a human Fc fragment and its complex with fragment B of protein A from *Staphylococcus aureus* at 2.9– and 2.8–Å resolution. Biochemistry. 20, 2361–2370.

Delaglio, F., Grzesiek, S., Vuister, G., Zhu, G., Pfeifer, J. and Bax, A. (1995), NMRpipe: a multidimentional spectral processing system based on UNIX pipes. J. Biomol. NMR 6, 277–293.

Foster, M.P., Wuttke, D.S., Clemens, K.R., Jahnke, W., Radhakrishnan, I., Tennant, L., Reymond, M., Chung, J. and Wright, P.E. (1998), Chemical shift as a probe of molecular interface: NMR studies of DNA binding by the three amino–terminal zinc finger domains from transcription factor IIIA. J. Biomol. NMR 12, 51–71.

(List continued on next page.)

*Primary Examiner*—Jill Warden
*Assistant Examiner*—Yelena Gakh
(74) *Attorney, Agent, or Firm*—Oblon, Spivak, McClelland, Maier & Neustadt, P.C.

(57) ABSTRACT

A method of identifying interface residues in a biomolecular complex are identified by selecting one molecule with residues to be identified, and the nonexchangeable hydrogens (protons) and not less than 70% of exchangeable hydrogens (protons) in the one molecule are exchanged to deuteriums, followed by positional identification of the exchangeable hydrogens (protons) which are located on this molecule within 10 angstrom (Å) from hydrogen (s) (proton (s)) in a neighboring biomolecule in the complex and are cross-saturated by cross-saturation phenomena through the interface in the complex. Using the inventive method, the contact interfaces of biomolecular complex such as protein—protein complexes can be identified more accurately and easily than traditional methods.

14 Claims, 20 Drawing Sheets

OTHER PUBLICATIONS

Gouda, H., Torigoe, H., Saito, A., Sato, M., Arata, Y. and Shimada, I. (1992), Three-dimentional solution structure of the B domain of staphylococcal protein A: comparisons of the solution and crystal structures. Biochemistry. 31, 9665–9672.

Gouda, H., Shiraishi, M., Takahashi, H., Kato, K., Torigoe, H., Arata, Y. and Shimada, I. (1998), NMR study of the interaction between the B domain of staphylococcal protein A and the Fc portion of immunoglobulin G. Biochemistry. 37, 129–136.

Jedenberg, L., Tashiro, M., Tejero, R., Lynos, B.A., Uhlén, M., Montelione, G.T., Nilsson, B. (1996), The mechanism of binding staphylococcal protein A to immunogloblin G dose not involve helix unwinding. Biochemistry 35, 22–31.

Kalk, A. and Berendsen, H.J.C. (1976), Proton magnetic relaxation and spin diffusion in proteins. J. Magn. Res., 24, 343–366.

Kupce. and Wagner, G. (1995), Wideband homonuclear decoupling in proteinspectra. J. Magn. Res. B. 109, 329–333.

Langone, J.J. (1982), Protein A of *Staphylococcus aureus* and related immunoglobulin receptors produced by streptococci and pneumonococci. Adv. Immunol. 32, 157–252.

Live, D.H., Davis, D.G., Agosta, W.C. and Cowburn, D. (1984), Long Range Hydrogen Bond Mediated Effects in Peptides: 15N NMR Study of Gramicidin S in Water and Organic Solvents. J. Am. Chem. Soc. 106, 1939–1943.

Paterson, Y., Englander, S.W. and Roder, H. (1990), An antibody binding site on cytochrome c defined by hydrogen exchange and two–dimensional NMR. Science. 249, 755–759.

Pervushin, K., Riek, R., Wider, G. and Wuetrich, K. (1998), Attenuated T2 relaxation by mutual cancellation of dipole–dipole coupling and chemical shift anisotropy indicates an avenue to NMR structure of very large biological macromolecules in solution. Proc. Nat. Acad. Sci. USA. 94, 12366–12371.

Pervushin, K., Wider, G. and Wuetrich, K. (1998), Single transition–to–single transition polarization transfer (ST2–PT) in [15N, 1H]–TROSY. J. Biomol. NMR 12, 345–348.

Salzmann, M., Pervushin, K., Wider, G., Senn, H. and Wuethrich, K. (1998), TROSY in triple–resonance experiments: new perspectives for sequential NMR assignment of large protiens. Proc. Natl. Acad. Sci. USA. 95, 13585–13590.

Salzmann, M., Wider, G., Pervushin, K., Senn, H. and Wuethrich, K. (1999), TROSY in Triple–Resonance Experiments For Sequential NMR Assignments of Large Proteins. J. Am. Chem. Soc. 121, 844–848.

Song, J. and Ni, F. (1998), NMR for the design of functional mimetics of protein–protein interactions: one key is in the building of bridges. Biochem. Cell Biol. 76, 177–188.

Torigoe H., Shimada, I., Saito, A., Sato, M. and Arata, Y. (1990), Sequential 1H NMR assignments and secondary structure of the B domain of staphylococcal protein A: structural changes between the free B domain in solution and the Fc–bound B domain in crystal. Biochemistry. 29, 8787–8793.

Venters, R.A., Huang C.C., Farmer II, B.T., Troland, R., Spicer, L.D. and Fierke, C.A. (1995), High–level 2H/13C/15N labeling of proteins for NMR studies. J. Biomol. NMR 5, 339–344.

Wang, Y.X., Jacob, J., Cordier, F., Wingfield, P.T., Palmer, I., Stahl, S.J., Lee–Huang, S., Torchia, D.A., Grzesiek, S., and Bax, A. (1999). Measurement of (3h)J(NC') connectivities across hydrogen bonds in a 30kDa protein. J. Biomol. NMR 14, 181–184.

Wells, J.A. (1991), Systematic mutational analysis of protein–protein interfaces. Methods Enzymol. 202, 390–411.

Wishart, D.S., Bigam, C.G., Yao.,J., Abildgaard, F., Dyson, H.J., Oldfield, E., Markley, J. and Sykes, B.D. (1995), 1H, 13C and 15N Chemical shift Referencing in Biomolecular NMR. J. Biomol. NMR 6, 135–140.

Zheng, J., Zabell, A.P.R., Post C.B., (1997), Corona: A Program to Analyze and Simulate NOESY Intensities by Matrix Methods for Multiple Spin Pair Interactions. Purdue University, West Lafayette.

de Vos, A.M., Ultsch, M., Kossiakoff, A.A. (1992), Human Growth Hormone and Extracellular Domain of Its Receptor: Crystal Structure of the Complex. Science 255, 306–312.

Akasaka, K. (1981), Longitudinal relaxation of protons under cross saturation and spin diffusion. J. Magn. Res. 45, 337–343.

Bax, A. and Subramanian, S. (1986), Sensitivity–Enhanced Two–Dimensional Heteronuclear Shift Correlation NMR Spectroscopy. J. Magn. Reson. 67, 565–569.

Clackson, T., Wells, J.A. (1995), A Hot Spot of Binding Energy in a Hormone–Receptor Interface. Science 267, 383–386.

Cunningham, B.C. and Wells, J.A. (1997), Minimized proteins. Curr. Opin. Struct. Biol. 7, 457–462.

Hideo Takahashi, et al., *A Novel NMR Method for Determining the Interfaces of Large Protein–Protein Complexes*, Nature Structural Biology, vol. 7, No. 3, Mar. 2000, p. 220–223.

* cited by examiner

CHEMICAL SHIFT PERTURBATION EXPERIMENT

H-D EXCHANGE EXPERIMENT

X-RAY CRYSTALLOGRAPHY

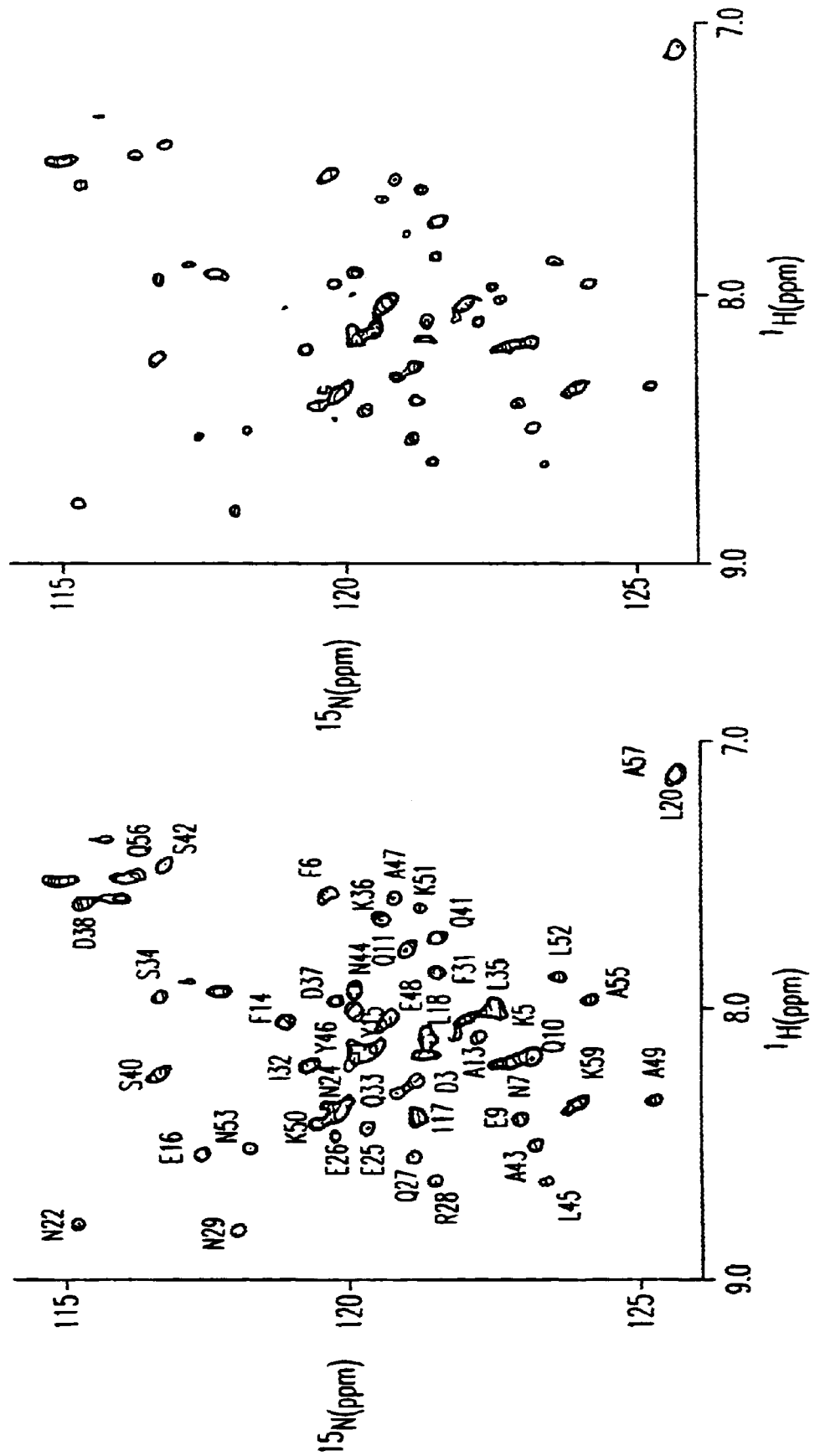

METHOD TO IDENTIFY INTERFACE RESIDUE IN BIOMOLECULAR COMPLEX

BACKGROUND OF THE INVENTION

1. Field of the Invention

The present invention relates to a method to identify an interface residue of a biomolecular complex, and provides a method for identifying the contact interface in a biomolecular complex accurately. By identifying residues at interface of a complex composed of biomolecules such as proteins, nucleic acids, etc., by the cross-saturation phenomena, the present invention makes it possible to identify the contact interface more accurately as compared to traditional methods.

2. Description of the Background

In living organisms, various molecular interactions take part in physiologic processes and comprise complicated networks. For example, such networks are observed in the immune system with antibodies and T lymphocytes, physiological regulation by hormones, gene expression by transcription factors, signal transmission pathways, etc. Revealing these networks of molecular interactions is an important goal in medicinal research because there are strong possibilities that the results will lead to the development of new medical treatment in the future. Furthermore, to identify various biomolecular interaction sites is expected not only to lead the investigation into physiological processes at molecular level, but also to provide important information for the design of novel drugs targeting the interaction sites (cf. De Vos et al., 1992; Song et al., 1998; Clackson et al., 1995).

One of the methods to identify the contact interface of complex is to determine the tertiary molecular structure using the X-ray crystallographic analysis. However, it is not always easy to use this method for the determination of large protein complex structures. Moreover, this method requires significant amounts of time. In another widely-used method, a combination of replacements of amino acid residues which comprise of the molecular surface and measurements of the binding activity gives only the indirect information about the binding site (cf. Wells et al., 1991; Cunningham et al., 1997).

On the other hand, in regards to NMR methods to identify the residues on the contact interface of biomolecular complex such as protein—protein complex, protein-nucleic acid complex, etc., the chemical shift peturbation (changes) of backbone amide groups upon the complex formation (cf. Foster et al., 1998) and the changes of the hydrogen-deuterium (H-D) exchange rates (cf. Paterson et al., 1990) have been used as the indicators.

For the purpose of illustration, a schematic drawing of protein A and immunoglobulin G are shown in FIG. 1. Protein A is an immunoglobulin binding protein that is a component of the cell wall of *Staphylococcus aureus*, and is known to bind specifically with the Fc region of immunoglobulin G (cf. Langone et al., 1982). The extracellular region of protein A is composed of five highly homologous and continuous Fc binding domains, which are called E, D, A, B, and C in order from the N-terminus (end). In addition, there is a cell wall-binding region called X on the C-terminus.

The tertiary structure of the B domain of protein A (FB) in solution has been determined by NMR. The important residues for the binding for the Fc fragment have been identified by the change of the H-D exchange rate and the chemical shift perturbation analyses (cf. Torigoe et al., 1990; Gouda et al., 1992; Gouda et al., 1998).

The three-dimensional structure of FB bound to the Fc fragment has previously been determined by X-ray crystallography (cf. Deisenhofer et al., 1981). In FIG. 2, the interaction interfaces determined by X-ray crystal structure, the H-D exchange experiments, and the chemical shift perturbation are shown. In this figure, CPK models of the FB that indicate the residues on the contact interfaces revealed by X-ray crystallography and the NMR methods are shown. A comparison of these residues indicates that distributions of the residues on the contact interfaces identified by the NMR methods are similar, but not identical, to those revealed by the X-ray crystallography. In particular, the changes in the chemical shifts and the H-D exchange rates induced by binding to the Fc fragment occur in some residues, which contain ones that do not exist on the contact interface revealed by the X-ray crystallography. The reason for the contradiction between the results obtained by the NMR methods and those obtained by the X-ray crystallography may be the result of the fact that changes in the chemical shifts and the H-D exchange rates are also affected by local environment and/or subtle conformational changes induced by the binding to the Fc fragment.

Thus, traditional NMR methods are insufficient for the accurate determination of the contact interface of a biomolecular complex, such as protein—protein complexes, and an alternative method is needed to identify accurately the contact interfaces.

SUMMARY OF THE INVENTION

It is an object of the present invention to provide a method of accurately determining the contact interfaces of biomolecular complexes by identifying the residues present at the contact interfaces.

In order to solve the problems described above, the present inventors, at first, have examined traditional methods in detail to develop a method for a more accurate determination of contact interfaces of biomolecular complexes. So far, for example, high resolution NMR methods have determined the contact interfaces of large protein—protein complexes (MW>50,000) using the changes in the chemical shifts and the H-D exchange rates induced by formation of the complexes as indicators (cf. Foster et al., 1998; Paterson et al., 1990). However, the interfaces determined by those methods were not always identical to those determined by X-ray crystallography, and there were many ambiguous points. It was found that these methods were limited, and did not always provide accurate analyses. As the result of extensive examination about the identification methods using NMR, it has been revealed that the contact interfaces of large protein—protein complexes can be determined more accurately by making use of the deuterium labeling and the cross-saturation phenomena. The present invention is based on this finding.

Accordingly, the present invention provides a method to identify interface residues in a biomolecular complex comprising at least two biomolecules, which comprises:

exchanging at least a portion of nonexchangeable hydrogens, i.e., protons and at least 70%, i.e., not less than 70%, of exchangeable hydrogens (protons) in one biomolecule component of the complex, respectively, to deuteriums; and identifying the position of exchangeable proton(s) which are located on this biomolecule which are present within 10 angstrom (Å) from hydrogen(s) (proton(s)) in a neighboring biomolecule in the complex and receive cross-saturation (are cross-saturated) by cross-saturation phenomena through the interface of the complex.

The present invention makes it possible to identify the contact interface of biomolecular complex more accurately as compared to traditional methods. In a case where the biomolecular complex consists of protein A and protein B, it is possible to determine the conformation (steric configuration) of protein A-protein B complex only on the basis of the conformations (steric configurations) of the each component protein. Furthermore, the minimum structural unit required for binding to protein B can be revealed by the identification of the contact interface of protein A.

Therefore, by mimicking this contact interface, it is possible to prepare a low molecular weight compound which can bind to a protein B. When protein B is a receptor, the low molecular weight compounds may function as an agonist or an antagonist. Thus, the information provided by the inventive method enables the production of new medicines. A particularly preferred embodiment of the present invention is a method to identify interface residues in a biomolecular complex, which comprises:

selecting from among plural biomolecules which compose a complex, one biomolecule with residues to be identified at the complex interface;

exchanging the nonexchangeable hydrogens (protons) and at least 70% (not less than 70%) of exchangeable hydrogens (protons) of the selected biomolecule, respectively, to deuteriums; and identifying the position of the exchangeable hydrogens (protons) which are located on this biomolecule within 10 angstrom (Å) from hydrogen(s) (proton(s)) in the neighboring biomolecule in the complex and receive cross-saturation (are cross-saturated) by cross-saturation phenomena through the interface of the complex.

In another embodiment, the present invention provides a method for identifying an exchangeable hydrogen atom present at the interface of a biomolecular complex, wherein the biomolecular complex comprises a first biomolecule and a second biomolecule, and wherein at least a portion of the nonexchangeable hydrogens and at least 70% of exchangeable hydrogens in the first biomolecule are exchanged to deuteriums, comprising:

irradiating the second biomolecule in the biomolecular complex; and identifying at least one exchangeable hydrogen atom in the first biomolecule of the biomolecular complex which receives cross-saturation from the irradiated second biomolecule.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Pulses are applied along the x direction, if not otherwise indicated. Narrow bars and wide bars indicate 90 degree (90°) pulses and 180 degree (1800) pulses, respectively. The line marked Gz indicates the duration and amplitude of the sine-shaped pulsed magnetic field gradient applied along the z-axis and the duration time, and each is in the followings: G1=600 μsec, 7.5 G cm$^{-1}$; G2=1000 μsec, 10 G cm$^{-1}$; G3=600 μsec, 14.5 G cm$^{-1}$; and G4=600 μsec, 20 G cm$^{-1}$. The delay time (Δ) is 2.25 msec. The following phase cycling scheme was used: $\phi1$={y, -y, x, -x}; $\phi2$={-y}; $\phi3$={-y}; $\phi4$={-x}; $\phi5$={-y}; $\phi6$(receiver)={y, -y}. In the $^{15}$N($t_1$) dimension, a phase-sensitive spectrum was obtained by recording a second FID for each increment of $t_1$, with $\phi1$={y,-y, x, -x}; $\phi2$={y}; $\phi3$={y}; $\phi4$={-x}; $\phi5$={y}; $\phi6$(receiver)={-x, x }, and the data were processed as described in the reference (cf. Pervushin et al., 1998).

Figures 5A, 5B:
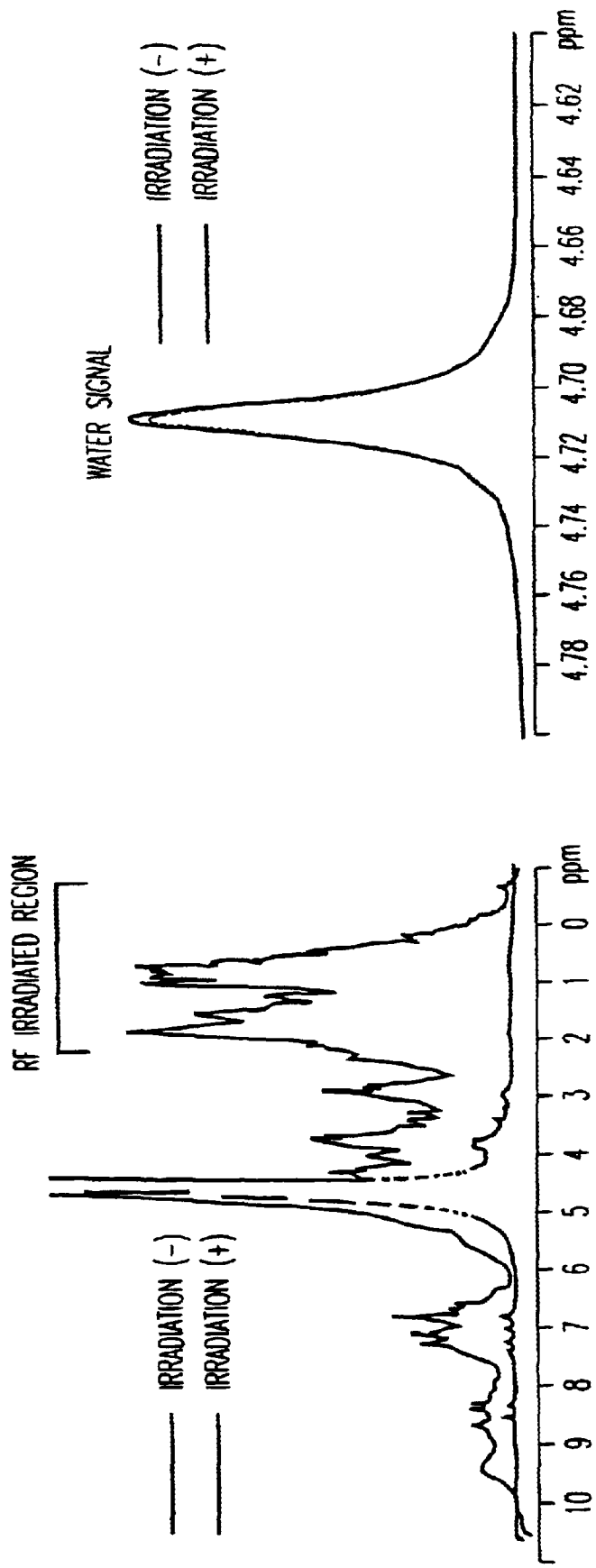

FIG. 5 shows the NMR spectrum used for confirmation of the selective radio frequency irradiations by $^{1}$H-1D NMR. FIG. 5(a): the spectra with and without radio frequency irradiations; FIG. 5(b): the enlarged part of water signal region of the above spectra. Irradiation(-): without irradiation; Irradiation(+): with irradiation.

Figure 6B:
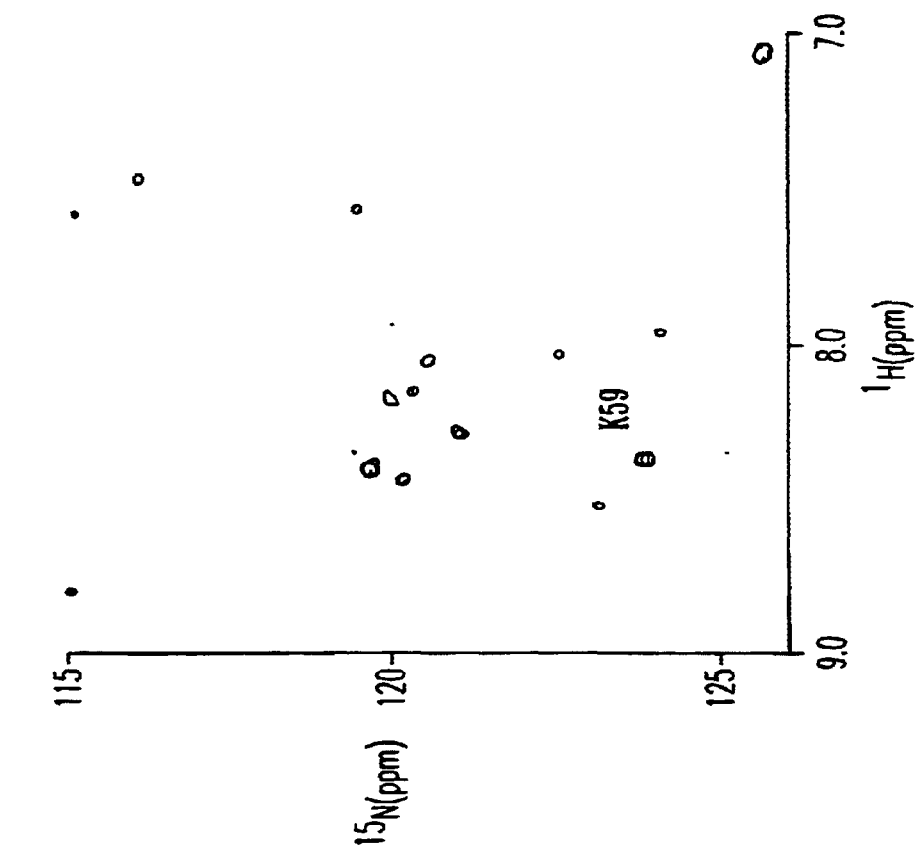
Figure 6A:
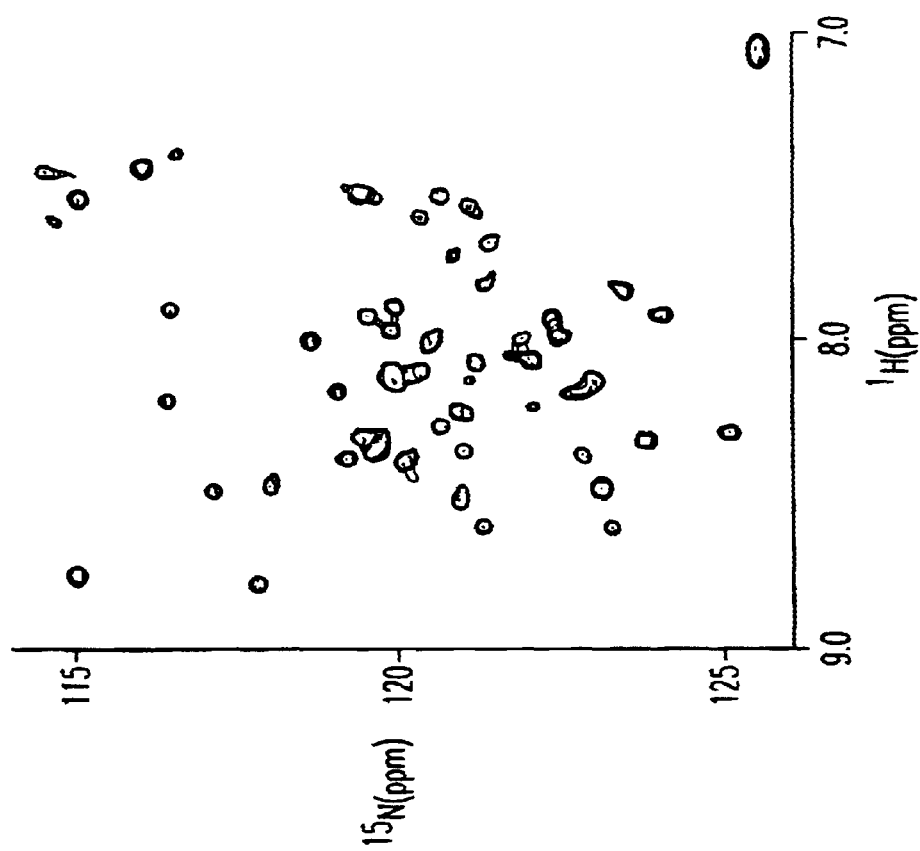

FIG. 6 shows the results of the cross-saturation experiment. FIG. 6(a): the spectrum without radio frequency irradiation (The intensity of radio frequency was set to 120 dB.); FIG. 6(b): the spectrum with radio frequency irradiation.

Figures 7A, 7B:
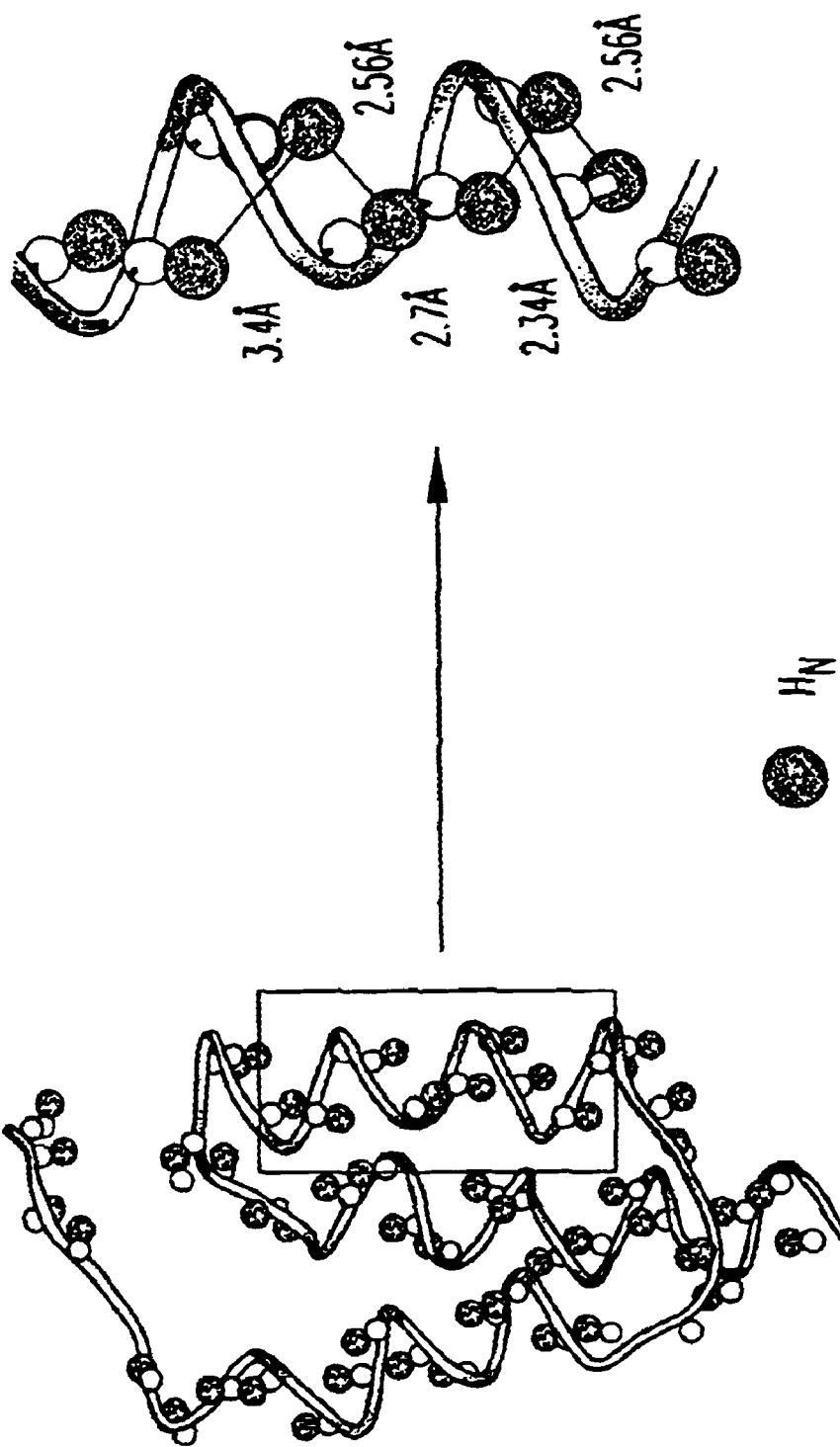

FIG. 7 shows a schematic illustration of distance among the amide protons in the FB molecule, where the Closed circle (•) represents HN (amide proton).

Figures 8A, 8B:
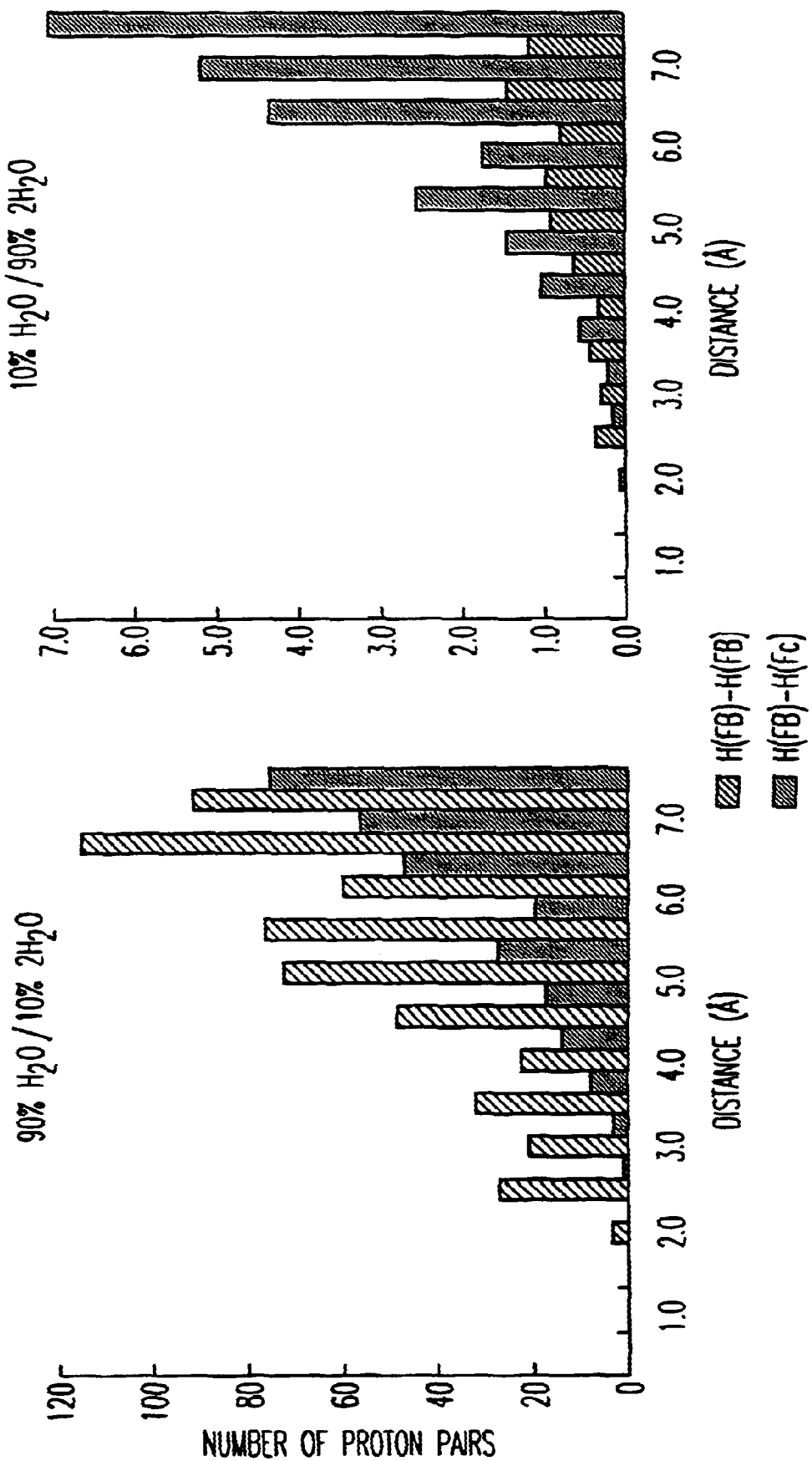

FIG. 8 shows distribution of the distances among protons in the FB-Fc complex. FB: labeled (deuterated); Fc: nonlabeled. Gray bars (left side of the pair of bars): H(FB)-H(FB); black bars (right side of the pair of bars): H(FB)-H(Fc).

Figure 9B:
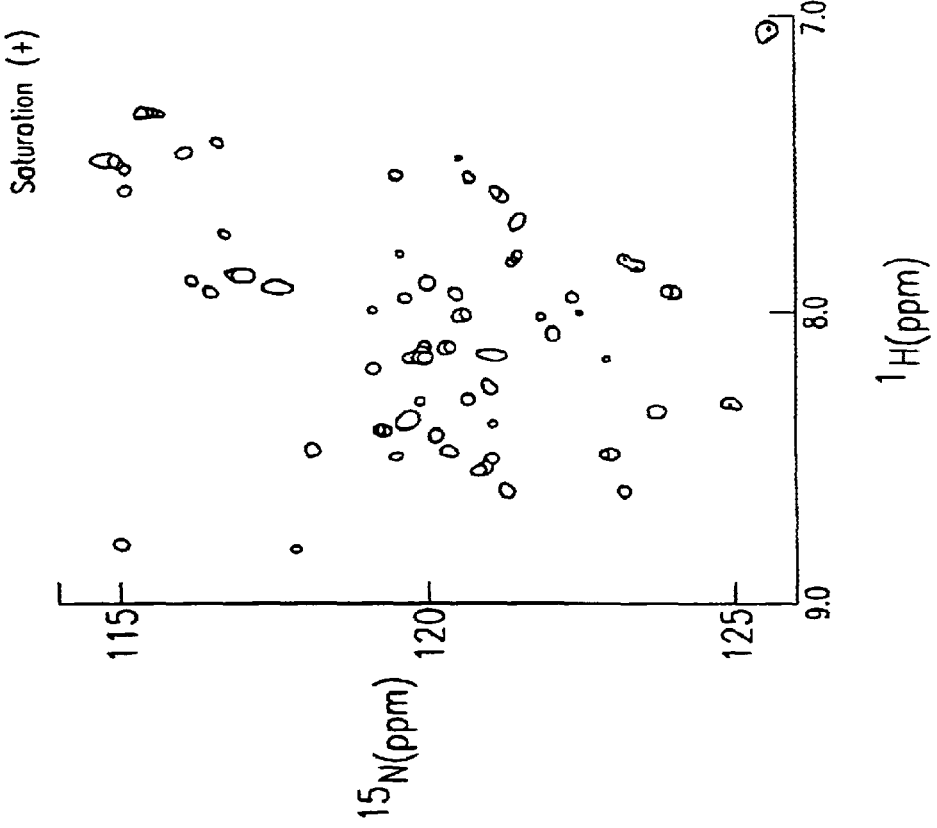
Figure 9A:
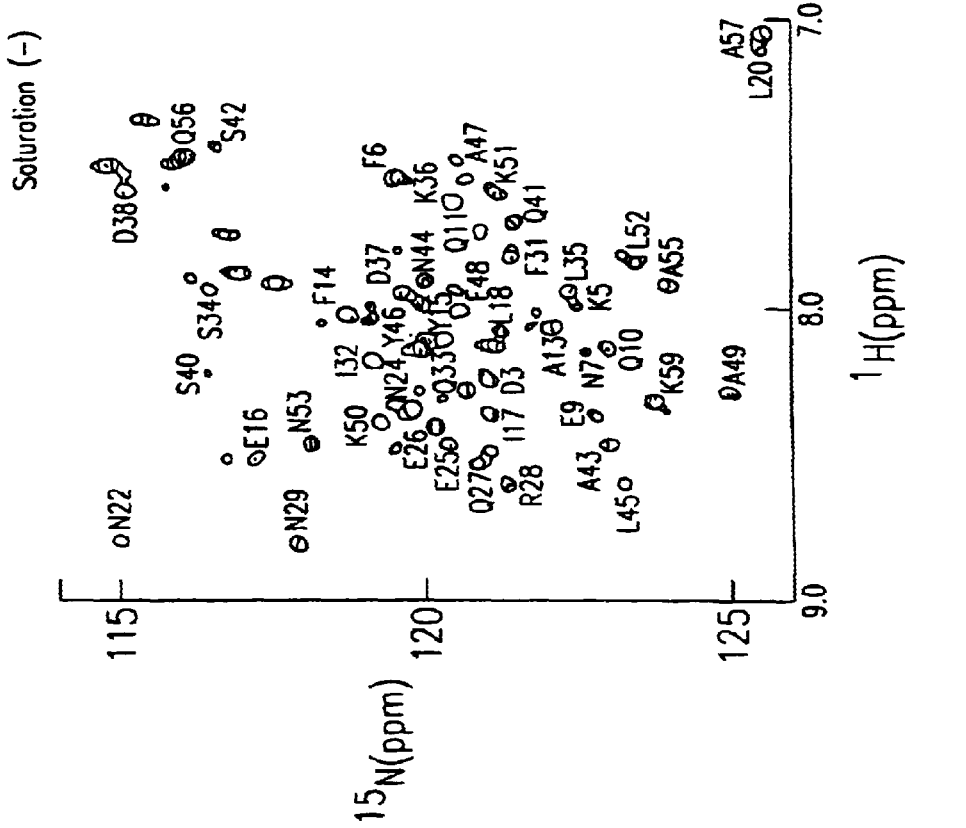

FIG. 9 shows the results of the cross-saturation experiment (10% $H_2O$/90% $^{2}H_2O$). The $^{1}$H-$^{15}$N TROSY-HSQC spectra observed for the complex between the doubly labeled FB and the nonlabeled Fc fragment in 10% $H_2O$/90% $^{2}H_2O$ as the water/deuterium oxide concentration in the solvent are shown. FIG. 9(a): the spectrum without a radio frequency irradiation (The intensity of radio frequency was set to 120 dB.); FIG. 9(b): the spectrum with a radio frequency irradiation.

Figure 10:
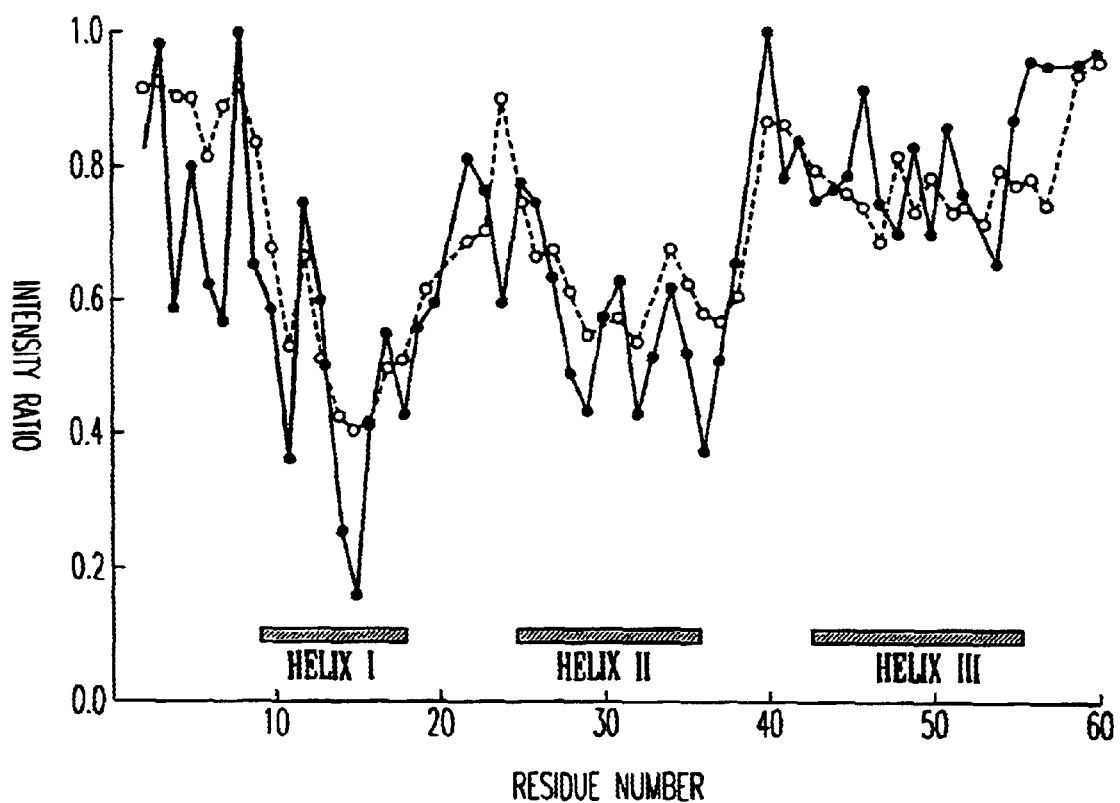

FIG. 10 shows plots of the signal intensity ratios of the crosspeaks in the cross-saturation experiments.

FIG. 11 shows a comparison of the Fc binding sites of the FB revealed by various methods. FIG. 11(a): the X-ray crystallography (X-ray crystal structure analysis); FIG. 11(b): the chemical shift perturbation; FIG. 11(c): the changes in the H-D exchange rate (experiments); FIG. 11(d): the cross-saturation (experiments).

Figure 12B:
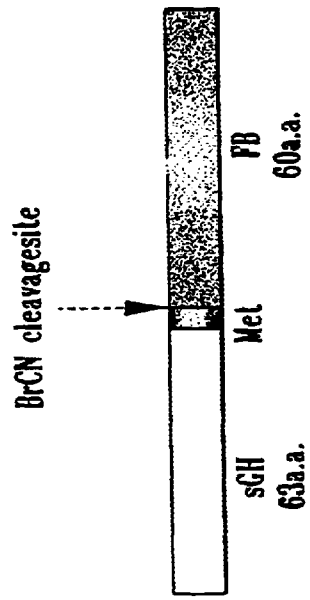
Figure 12A:
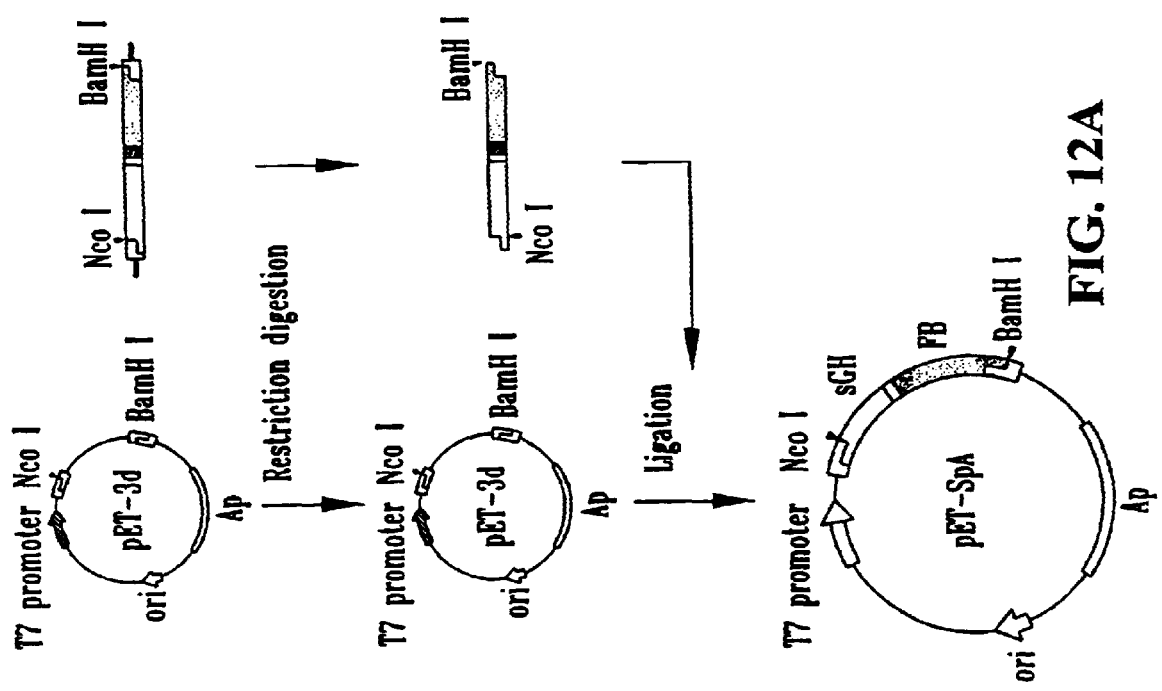

FIG. 12 shows construction of E. coli expression system of the FB fragment of protein A, and the gene product. FIG. 12(a): concept of structural scheme of pET-SpA; FIG. 12(b): chart of protein expressed by pET-SpA.

Figure 13A:
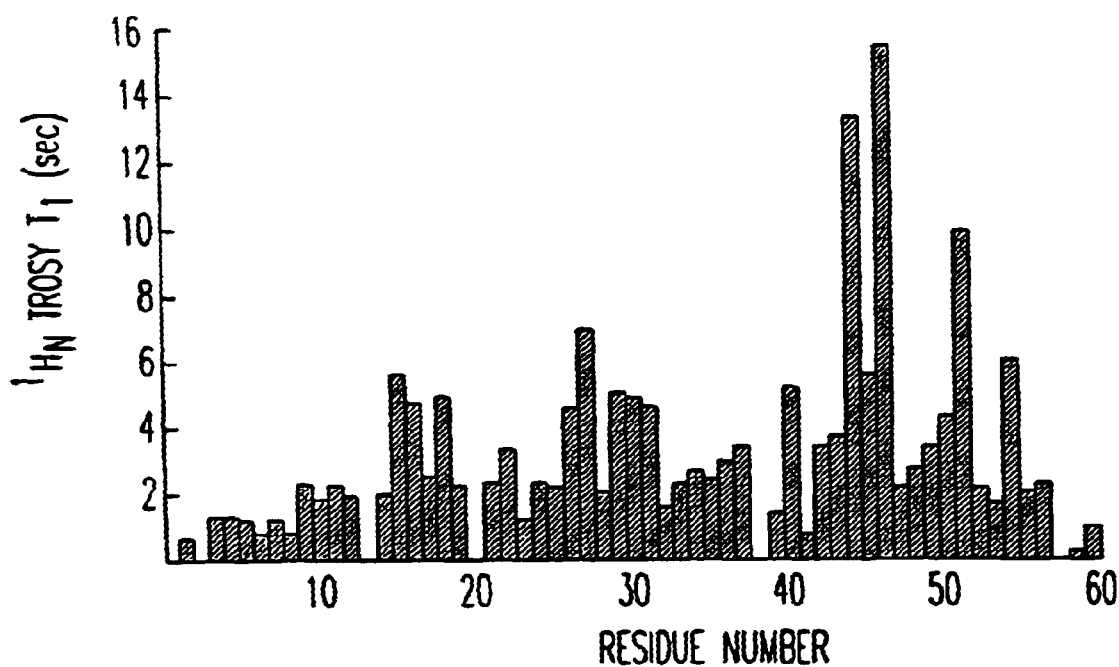
Figure 13B:
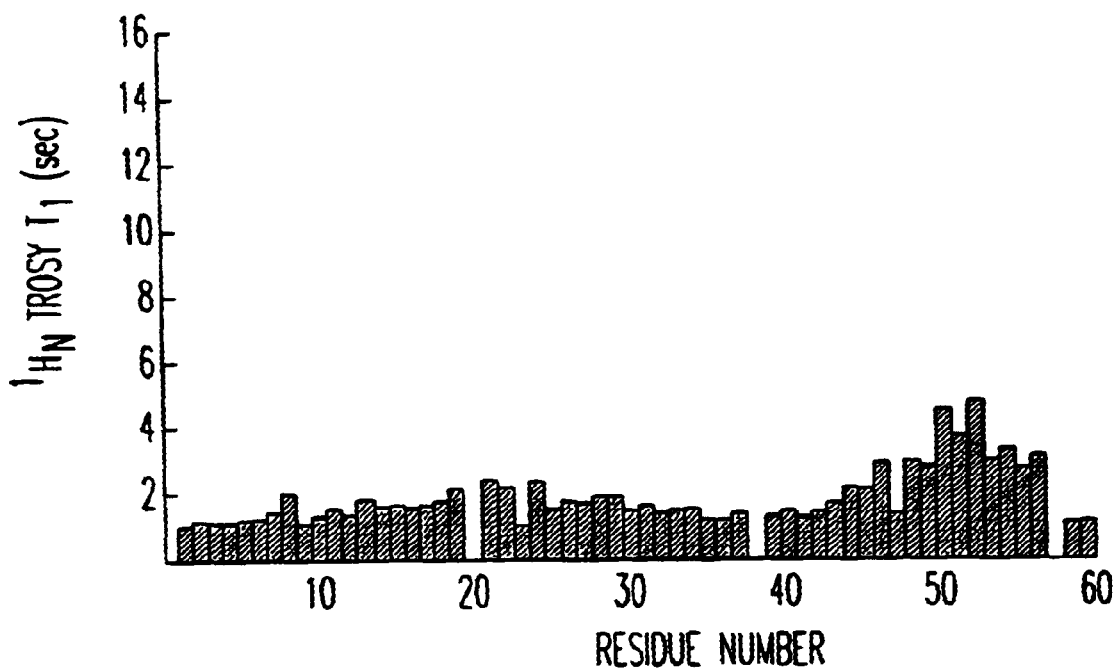

FIG. 13 shows relaxation times of the FB uniformly labeled with 98% $^{2}$H/$^{15}$N in complex with the unlabeled Fc fragment. FIG. 13(a): the case where the concentration of the water (light water) in the solvent is 10%; FIG. 13(b): the case where the concentration of the water in the solvent is 90%.

Figure 14:
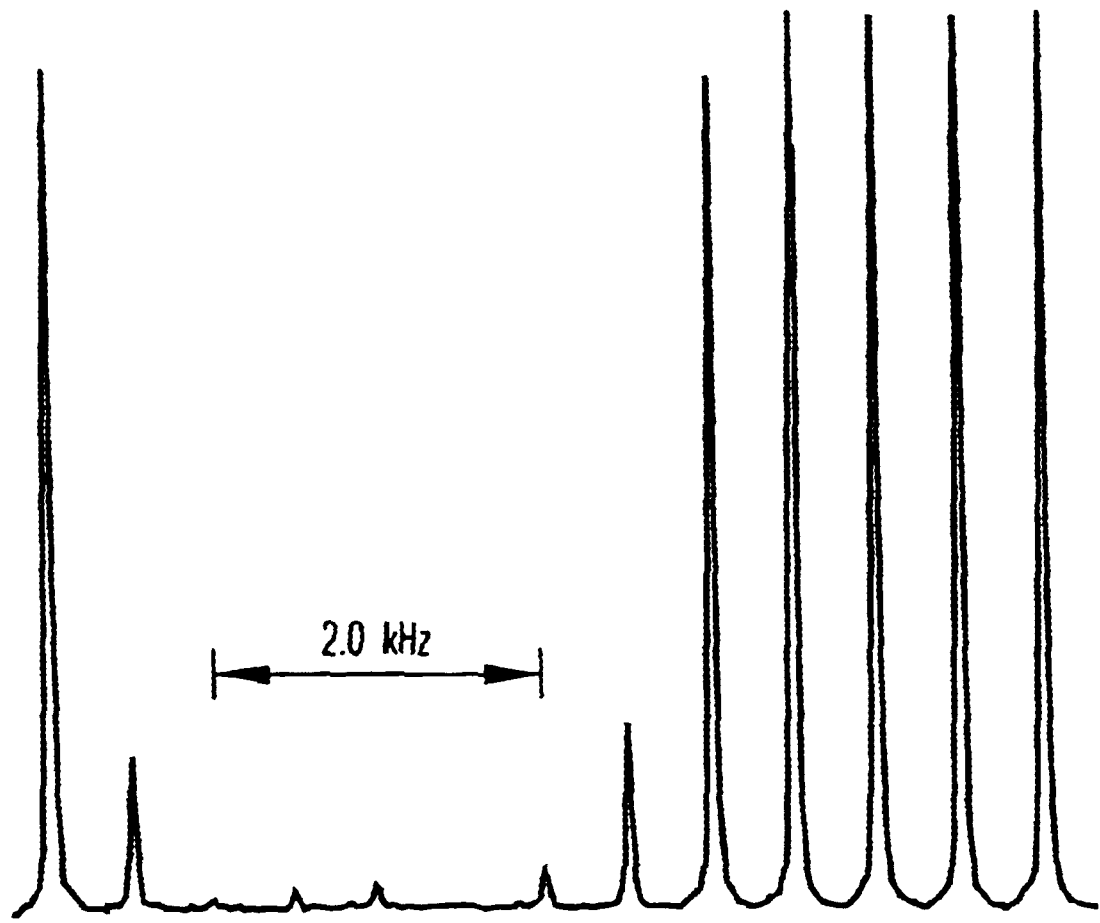

FIG. 14 shows a band of radio frequency used for the cross-saturation.

Figure 15:
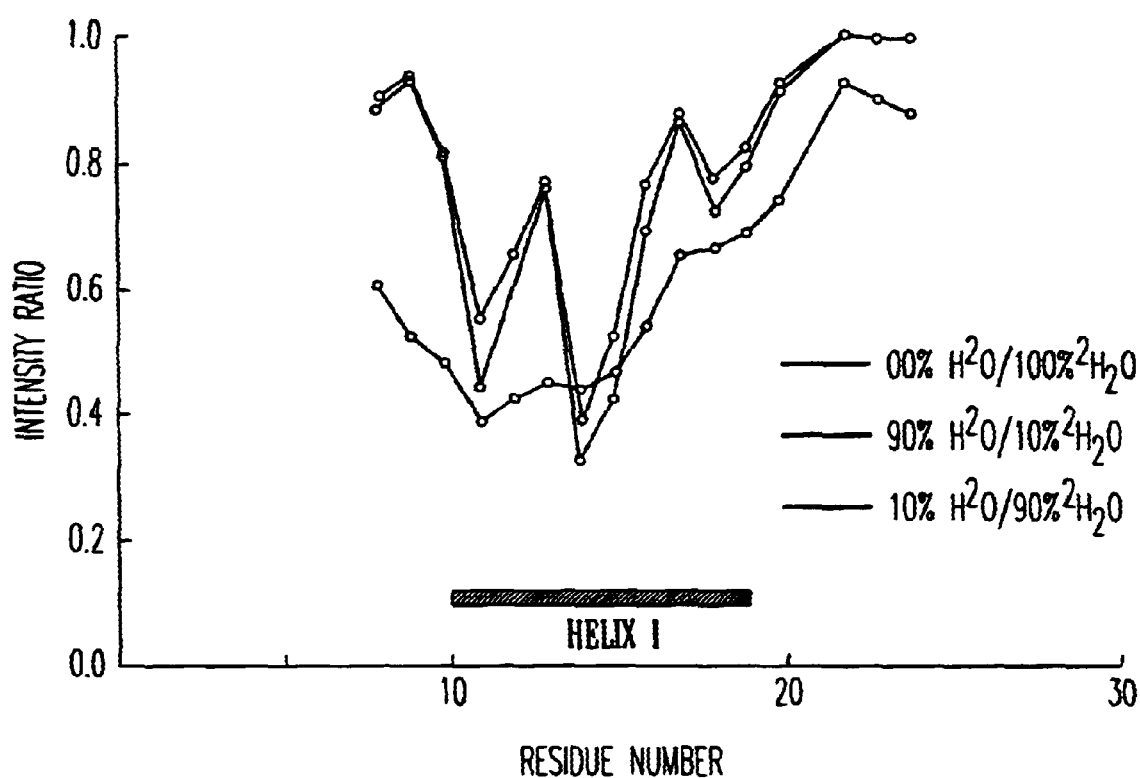

FIG. 15 shows a simulation of the cross-saturation.

Figure 16:
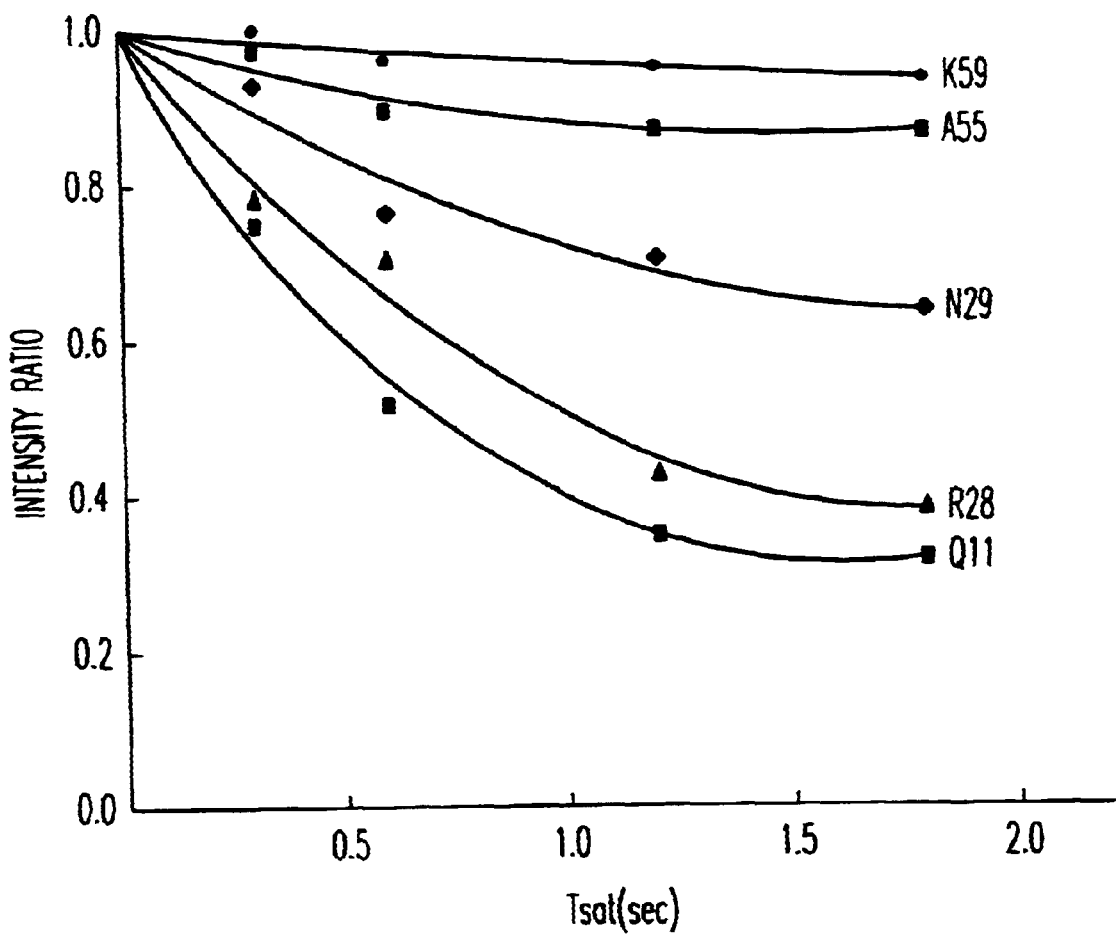

FIG. 16 shows changes in signal intensity with the saturation time ($T_{sat}$).

Figure 17A:
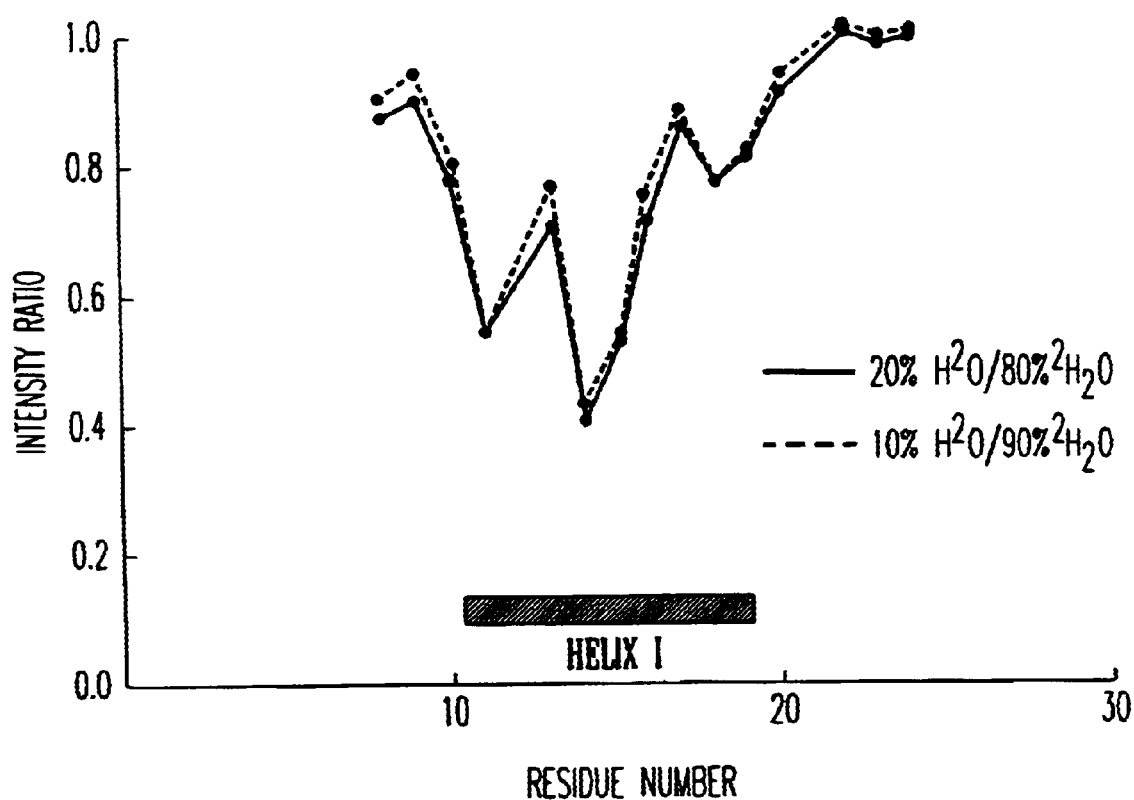
Figure 17B:
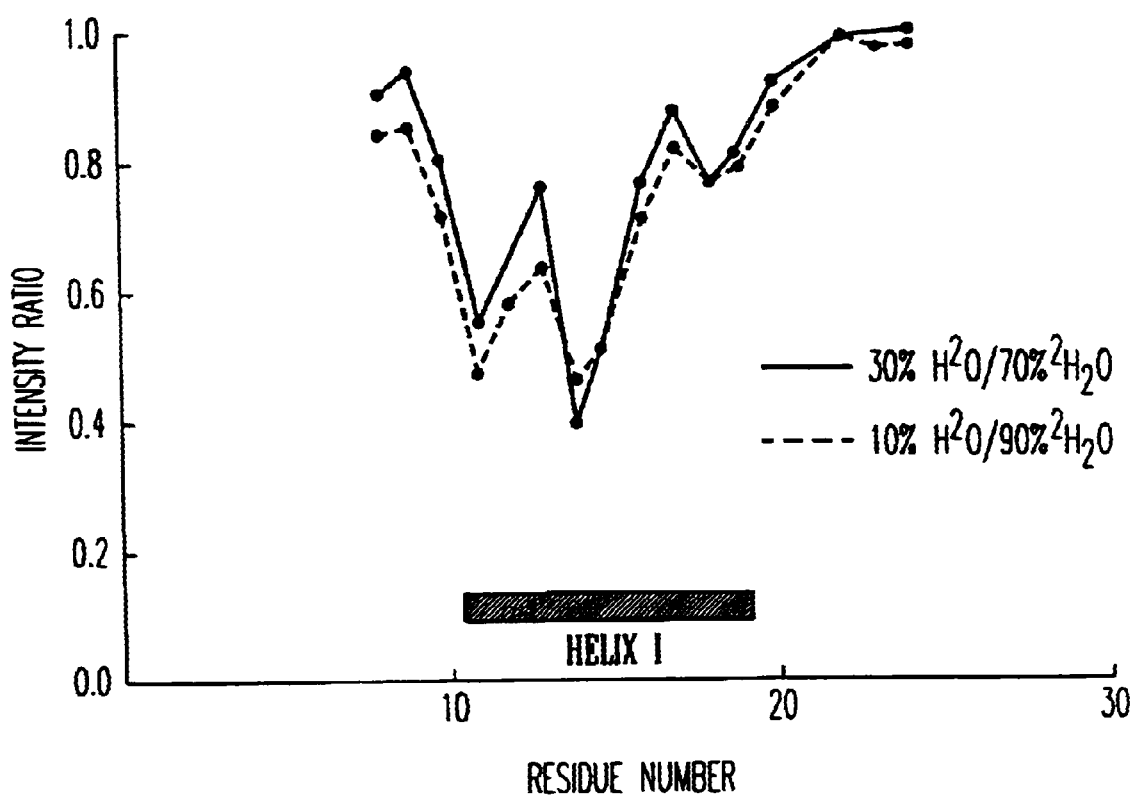

FIG. 17 shows effects of $H_2O$ concentration in solvent on the cross-relaxation. FIG. 17(a): comparison between 20% $H_2O$/80% $^2H_2O$ (solid line) and 10% $H_2O$/90% $^2H_2O$ (dotted line); FIG. 17(b): comparison between 30% $H_2O$/70% $^2H_2O$ (solid line) and 10% $H_2O$/90% $^2H_2O$ (dotted line).

FIG. 18 shows spectra showing the result of the cross-saturation (20% $H_2O$/80% $^2H_2O$). FIG. 18(a): the spectrum without irradiation of the radio frequency; FIG. 18(b): the spectrum with irradiation of the radio frequency.

Figure 19:
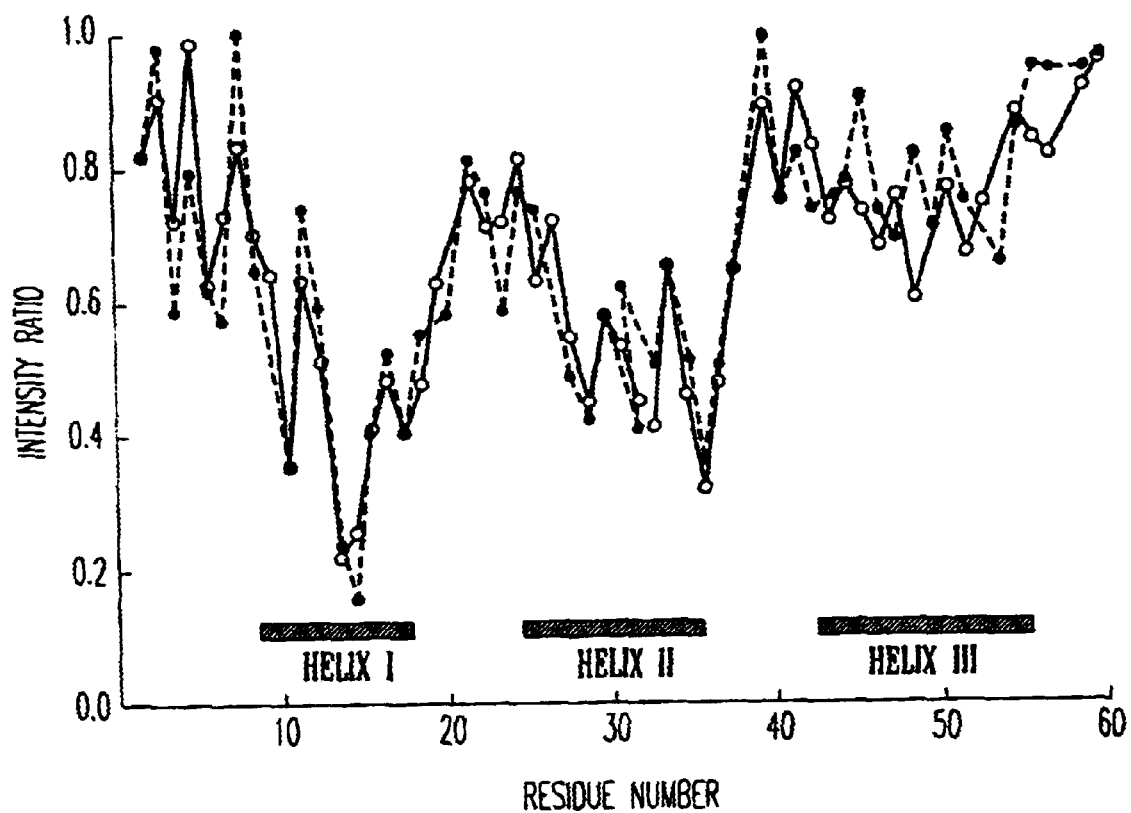

FIG. 19 shows plots of the signal intensity ratios of the crosspeaks in the cross-saturation experiments (20% $H_2O$/80% $^2H_2O$) are shown in a solid line: 20% $H_2O$/80% $^2H_2O$; dotted line: 10% $H_2O$/90% $^2H_2O$.

DETAILED DESCRIPTION OF THE INVENTION

The inventive method described herein makes use of the cross-saturation phenomena. Because the phenomena are strongly dependent on the space distance between two neighboring molecules, this method can determine the contact interface more accurately than the traditional method can do.

Without being limited to any particular thereof, the basis of the method is thought that exchangeable protons such as amide protons located around the contact interface of the target biomolecule receive the saturation transfer through the interface in the complex in the mechanism of the cross relaxations with the saturated protons in the neighboring biomolecule.

Biomolecules are macromolecules such as proteins, nucleic acids, and lipids which are present in living bodies of animals, plants, microorganisms, etc. With regard to the molecular weight, for example, the sizes are 10,000 or more as complexes, and are 2,000 or more as biomolecular components of the complexes. The nucleic acids include DNA and RNA. The complexes include protein—protein, nucleic acid-nucleic acid, protein-nucleic acid, protein-lipid complexes, and the likes. The protein—protein, nucleic acid-nucleic acid, protein-nucleic acid, and protein-lipid complexes are assemblages composed of more than two proteins, more than two nucleic acids, protein(s) and nucleic acid(s), and protein(s) and lipid(s), respectively. Each component binds together by non-covalent bonds. There is no limitation on the number of the component molecules of the complex.

The nonexchangeable hydrogens (protons) are protons that cannot be exchanged to hydrogens (protons) of solvent water, for example C—H protons. The exchangeable protons are protons that can be exchanged to protons of solvent water, for example N—H, O—H, or S—H protons.

There is no particular difficulty in exchanging nonexchangeable hydrogens (protons) in biomolecules to deuteriums, and known method to exchange nonexchangeable hydrogens (protons) to deuteriums can be used for the purpose. In brief, it can be done in a way that microorganisms which express the objective biomolecules are cultivated using media including deuterated components (deuterium-labeled components). For example, deuterium-labeled biomolecules can be recovered or prepared from bacterial cells cultivated in the medium including deuterium-labeled glucose or deuterium labeled acetic acid as the medium components dissolved in deuterium oxide. It is desirable that the deuterium exchange ratio of nonexchangeable protons is at least 80%, namely 80% or more. Synthesizing biomolecules from deuterium-labeled amino acids or deuterium labeled nucleic acids may also be performed.

To deuterate X% of exchangeable hydrogens (protons), deuterium oxide/water ratio of the solvent is set to X/(100-X). In this case, the water content corresponds to (100-X) %. For the determination of a contact interface by the present invention, to deuterate 70% or more of the exchangeable hydrogens (protons) is required, and, in that case, the X value is seventy or over seventy. In the present invention, 70% or over 70% of the deuteration ratio is sufficient. However, for prevention of excessive transfer of the cross-saturation, about 80~90% of the deuteration ratio is preferably used. In this case, 80~90 is used as the X value, and the deuteration can be readily accomplished. In this way, the method for the deuteration itself has no particular difficulty, and the deuteration can be easily achieved by making use of conventional or traditional methods.

The cross-saturation described above is an NMR phenomena, and occurs through a spin—spin interaction between a pair of proton nuclear magnetizations. For example, in the case of a complex composed of two molecules (components), a component receives the cross-saturation from the other component. Hydrogen (Proton) atoms of the other component that receives the cross-saturation are found to be located on the contact interface of the complex. To cause and make the cross-saturation, NMR pulses can be used. In this case, the cross-saturation can be made by selective irradiations of NMR pulse to hydrogen (proton) atoms that cause signals at particular regions (a partial region) of the NMR spectrum.

In the present invention, because nonexchangeable protons of the target biomolecule with interface residues to be identified are deuterated, the exchangeable protons of the target biomolecule that are located within 10 angstrom (Å) from protons of the other biomolecule adjacent to the target biomolecule receive the cross-saturation. Then, the types and the orders from N-terminus (in case of protein), or those from 5'-end (5'-terminus) (in case of nucleic acid)) of residues including these protons can be determined. Therefore, the residues on the contact interface (interaction interface) and/or the contact interface itself of the target molecules can be accurately determined and identified.

Moreover, by making use of the adiabatic shaped-pulse, the weak power of radio frequency can efficiently achieve the saturation. The band selective application of radio frequency makes it possible to saturate, for example, only the nonexchangeable protons. Therefore, to deuterate nonexchangeable protons of one component of biomolecular complex makes it possible to selectively saturate only the protons of the other component, and the induced cross-saturation make it possible to determine the residues on the contact interface of the biomolecular complex. For the band-selective saturation, an adiabatic shaped-pulse of the WURST-2 type (cf. Kupce, et al., 1995) is suitable, but the other type of pulse also can be used.

In the present invention, the fact that the deuteration ratio of the above exchangeable protons is 70% or over 70% has made it possible to develop the method for the accurate identification of residues on the contact interface. Some trials for the identification through the cross-saturation without the deuteration have been already done, but, because the cross-saturation diffuses through neighboring proton atoms, the identifications cannot be achieved so accurately as can be achieved by the method described herein.

The present invention is explained in more detail in the following sections.

Principles of the Present Invention

Figure 1A:
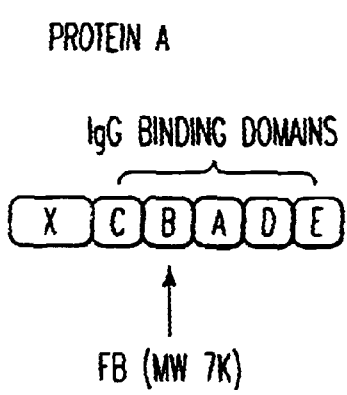
FIG. 1 shows schematic illustrations (simplified structural models) of protein A and immunoglobulin G; (a): protein A.
FIG. 1(b): immunoglobulin G.
Figure 1B:
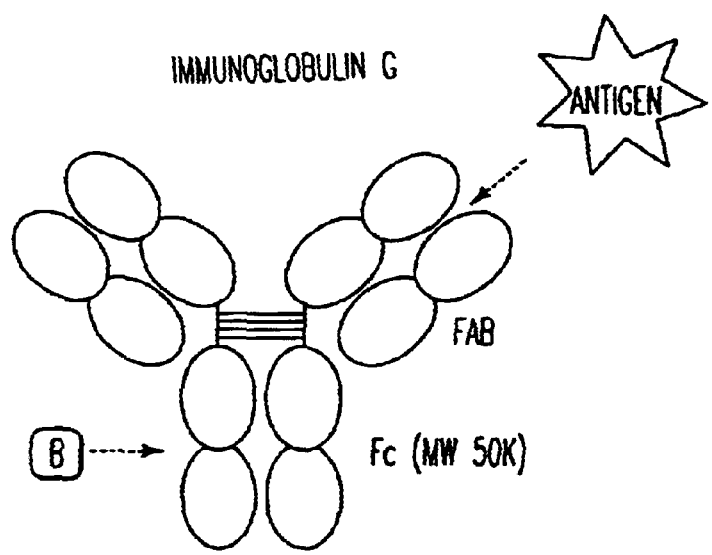
Figure 2A:
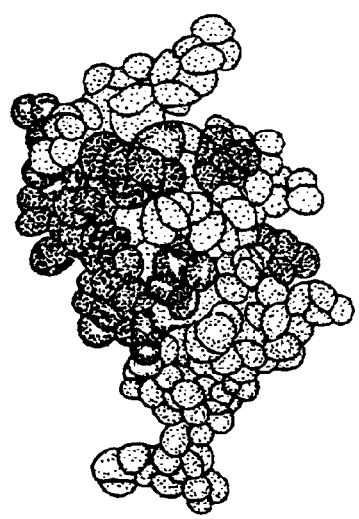
FIG. 2(a): results of the chemical shift perturbation analyses.
Figure 2B:
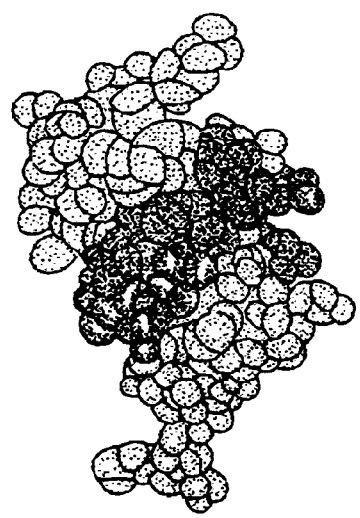
FIG. 2(b): results of the analysis with H-D exchange experiments; and (c): results of X-ray crystal structure analysis (X-ray crystallography study).
Figure 2C:
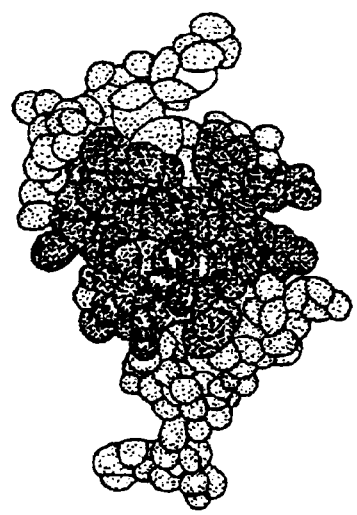
FIG. 2 shows contact interfaces of the FB molecule for binding to the Fc fragment are shown on the tertiary structural models.
Figure 3:
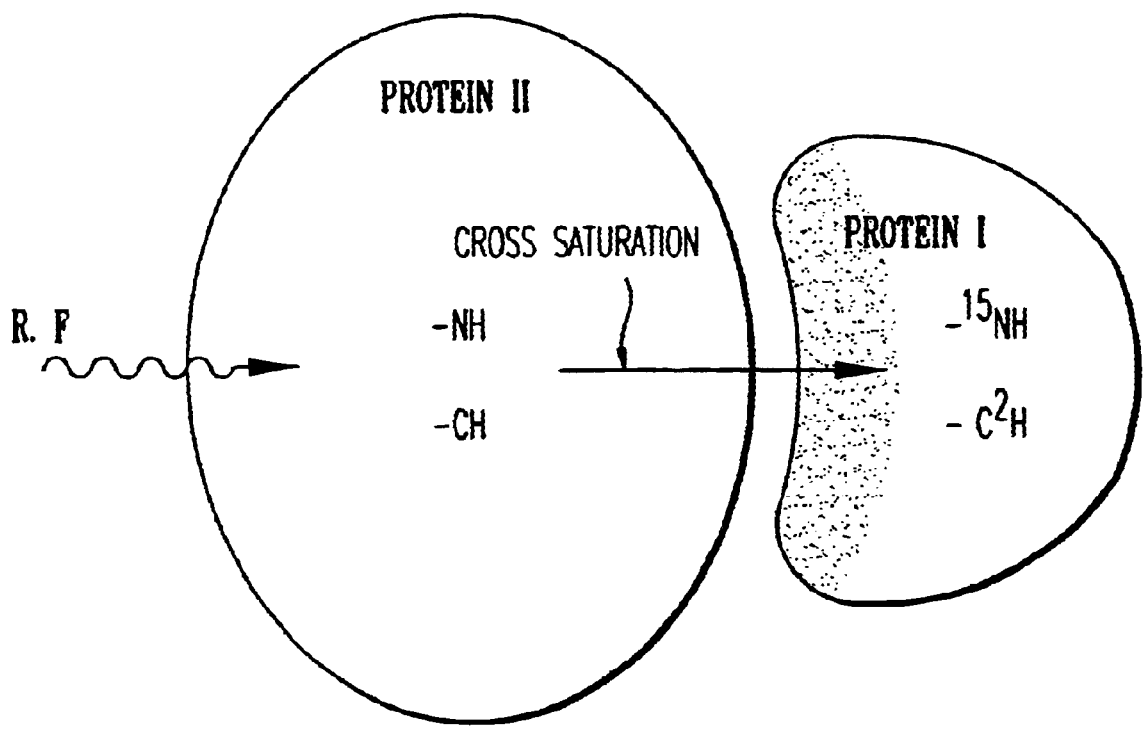
FIG. 3 shows the concepts of the cross-saturation developed by the present inventors, where R.F. is radio frequency.

In FIG. 3, features of the cross-saturation are shown, and the principles of the inventive method are illustrated in this figure.

The protein I for which it is desired to identify the interaction interface (interface residues) is uniformly labeled with $^2H$ and $^{15}N$ and then complexed with a nonlabeled target protein II. Accordingly, the complex is composed of molecules with lower (protein I) and higher (protein II) proton densities.

In the case of the protein with higher proton density, if the aliphatic proton resonances are irradiated non-selectively using a radio frequency (RF) field, not only its aliphatic resonances but also its aromatic and amide ones are instantaneously saturated. This phenomenon is well-known as the spin diffusion effect (cf. Kalk et al., 1976; Akasaka, 1981). Although the protein uniformly labeled with $^2H$ and $^{15}N$ is not directly affected by the RF field, it is expected that the saturation can be transferred from the target molecule (protein II) to the doubly labeled molecule (protein I) by cross relaxation through the interface of the complex. If the proton density of the doubly labeled molecule is sufficiently low, then the saturation transferred to it is limited to the interface. One can, therefore, identify the residues at the interface of protein I by observing the reductions of the peak intensities in the $^1H$-$^{15}N$ HSQC spectra.

Pulse Sequence for the Cross-Saturation Method.

Figure 4:
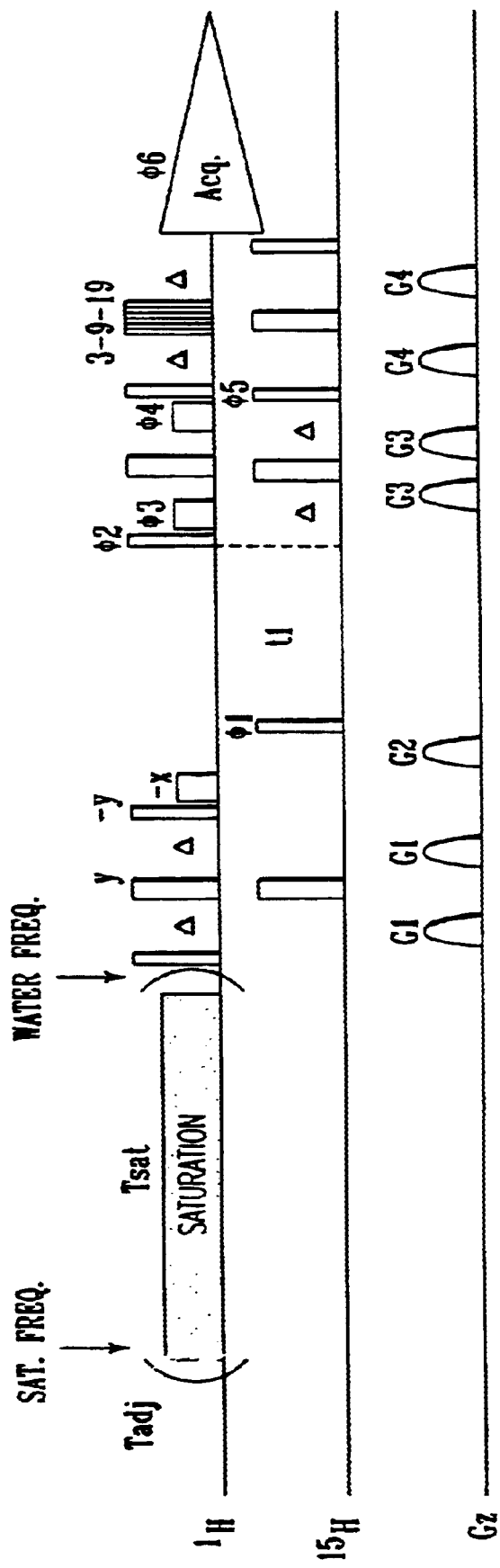
FIG. 4 shows a NMR pulse scheme used for the cross-saturation method developed for use in the method of the present invention.

FIG. 4 is a pulse scheme used for the cross-saturation method developed for the present invention. It consists of an alternative band selective WURST-2 type adiabatic shaped-pulse (cf. Kupce, et al., 1995) followed by a water flip-back type TROSY-HSQC pulse scheme (cf. Pervushin, et al., 1998; Pervushin, et al., 1998). By the application of the composite pulse decoupling method with the WURST-2 adiabatic shaped-pulse to the saturation of the aliphatic protons, even with the low power, the radio frequency field can efficiently achieve the saturation in the adiabatic pulse.

Confirmation of the Selective Radio Frequency Irradiations by $^1H$-1D NMR

As shown in FIG. 5, the saturation of Fc fragment was confirmed by the $^1H$-1D NMR spectrum. FIG. 5(a) is a $^1H$-1D NMR spectrum which was obtained just after the proton magnetization of the sample consisted of only the nonlabeled Fc fragment was saturated by the WURST-2. It is found that, by using the alternative band selective WURST-2 type saturation scheme, the saturation of proton magnetization in the aliphatic proton region is achieved sufficiently, and the saturation extends to the aromatic and amide proton regions due to the spin diffusion.

On the other hand, FIG. 5(b) is an enlarged part of water signal region of the spectrum shown in FIG. 5(a). The result that, by comparison with a spectrum without the irradiation using a radio frequency field, almost no change of intensity of the water signal is observed indicates that this saturation method has a very high selectivity for the aliphatic proton region, and that no direct radio frequency irradiation to the water signal arises (Additional information 2 (The band of radio frequency field (stretched adiabatic pulse WURST2) used for the cross-saturation)). Namely, it is found that, when FB-Fc complex is irradiated using the radio frequency field in this way, not only the amide protons of FB are not saturated directly, but also amide protons which are exchanged to water rapidly is not affected by the irradiation.

Application to the FB-Fc Complex of the Cross-Saturation.

The measurement method described above was applied to $^2H$, $^{15}N$-labeled FB in complex with a nonlabeled Fc fragment. FIG. 6 shows the results of the cross-saturation experiment. The $^1H$-$^{15}N$ TROSY-HSQC spectra observed for the complex between the doubly labeled FB and the nonlabeled Fc fragment, without and with the irradiation, respectively, are shown in FIGS. 6(a) and 6(b). FIG. 6(a) is a spectra without radio frequency irradiations, and FIG. 6(b) is a spectra with radio frequency irradiations.

As shown in FIG. 6(a), almost all of the separate crosspeaks originating from the amide groups of the FB bound to Fc were detected, and the assignments for the crosspeaks were successfully established using triple resonance TROSY experiments (cf. Salzmann et al., 1998; Salzmann et al., 1999) (Additional information 3 (The assignments for NMR signals of the FB)).

The effect of the irradiation with a saturation time of 1.2 s on the FB molecule in the complex is clearly observed in FIG. 6(b). The intensities of almost all crosspeaks were obviously reduced by the irradiation. This indicates that saturation in the Fc fragment in the complex was transferred to the bound FB through the interface. However, the reduction of the intensities occurred almost uniformly at each amide groups. The reason is thought that the saturation transfer from the Fc fragment was not restricted on the contact interface, and the whole FB molecule was saturated uniformly through the spin diffusion occurred at the inside of the FB molecule.

The Effect of the Spin Diffusion in the FB Molecule

The efficiency of the suppression of the spin diffusion in the FB molecule depends on the concentration of light water ($H_2O$) in the sample solution (solvent). The conformation of the FB molecule in the complex is a bundle of three α-helices (cf. Gouda et al., 1992; Gouda et al., 1998; Jedenberg et al., 1996). Therefore, in the case of 90% $H_2O/10\%$ $^2H_2O$ being a light water/deuterium oxide concentration of the solvent in the sample, which is conventionally used for NMR spectroscopy, the amide proton of the deuterated FB at the $i^{th}$ position is spatially close (within 4 angstrom (Å)) to those at the i−1 and i+1 positions (see FIG. 7 (chart of distance among protons in the FB molecule)). Because, in that case, there is the strong dipole—dipole interaction between the intramolecular amide protons, the situation in which the intramolecular spin diffusion readily occurs is imagined.

On the basis of the simulation of the cross-saturation phenomenon, in 10% $H_2O/90\%$ $^2H_2O$, the amide proton of the deuterated FB exists in virtual isolation from the other amide protons to the extent (level) that the interaction between spins can be ignored, and the effect of spin diffusion on the bound FB is thus effectively suppressed (the simulation of the cross-saturation described later). Namely, only the sufficient deuteration of the exchangeable protons of the FB molecule makes it possible to detect specially and specifically the intermolecular cross-saturation phenomenon (see FIG. 8 (distribution of the distances among protons in the FB-Fc complex). It is to be noted that if the concentration of protein is proper (0.5~1.0 mM), the TROSY-HSQC spectrum can be observed and obtained within a reasonable measurement time (~24 hrs) in the solvent condition described herein.

Application to the FB-Fc Complex of the Cross-Saturation (10% $H_2O/90\%$ $^2H_2O$)

FIG. 9 shows the results of the cross-saturation experiment (10% $H_2O/90\%$ $^2H_2O$). The $^1H$-$^{15}N$ TROSY-HSQC spectra observed for the complex between the doubly labeled FB and the nonlabeled Fc fragment in 10% $H_2O$/ 90% $^2H_2O$ being a light water/deuterium oxide concentration of the solvent without and with radio frequency irradiation are shown in FIGS. 9(a) and 9(b), respectively.

The effect of the irradiation with a saturation time of 1.2 s on the FB molecule in the complex is clearly observed in FIG. 9(b). The intensities of some crosspeaks were obviously reduced by the irradiation. This indicates that saturation in the Fc fragment in the complex was transferred to the FB molecule in the Fc bound state through the interface. However, as compared with the case in which the solvent water (light water)/deuterium oxide ratio is 90% $H_2O$/10% $^2H_2O$, it is clear that each change of the signal intensity varies widely.

Result of the Cross-Saturation

FIG. 10 (plots of the signal intensity ratios of the crosspeaks in the cross-saturation experiments) is a graph in which the intensity ratio of the crosspeaks observed with irradiation to those without irradiation is plotted for residue number of the FB. Under the condition of 10% $H_2O$/90% $^2H_2O$, small intensity ratios are specifically observed for the residues in helix I (Gln10-His19) and helix II (Glu25-Asp37) (see FIG. 10). In addition, interestingly, the values of the ratios for helices I and II are smaller for every third or fourth residue (Gln 11, Tyr15 and Leu18 in helix I, and Asn29, Ile32 and Lys36 in helix II), suggesting that one side of each of the helices is responsible for binding the Fc Fragment. These results are in agreement with the X-ray crystallography studies (information from X-ray crystal structure analysis).

The same plots were prepared for the results obtained in the experiment carried out under the condition of 90% $H_2O$/10% $^2H_2O$, being the solvent water (light water)/ deuterium oxide ratio. The profile of the plots showing the signal intensity ratio for the helical region no longer exhibits any distinctive pattern due to spin diffusion. Particularly in the helix region in which the distances among the amide protons are very short, two adjacent amino acid residues show almost same changes of the signal intensity (see FIG. 10, dotted line) by comparison with the results obtained in the 10% $H_2O$/90% $^2H_2O$ condition. Thus, it can be concluded that the cross-saturation can be observed so long as the concentration of $H_2O$ (light water) in the solvent is low enough.

Comparison of the Fc Binding Sites of the FB

FIG. 11 shows a comparison of the Fc binding sites of the FB. In this figure, the Fc binding sites of the FB determined by X-ray crystallography (crystal structure analysis) are compared with those determined by the NMR methods including the cross-saturation method.

Figure 11A:
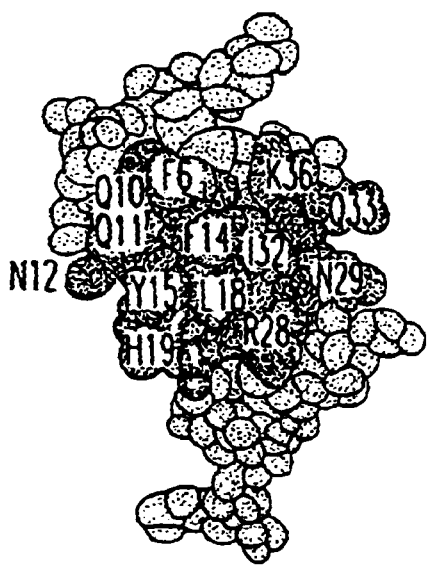

In FIG. 11(a), residues with accessible surface areas that are indicated by X-ray crystallography (crystal structure) to be covered upon binding of the Fc fragment are mapped on the molecular structure of the FB (cf. Gouda et al., 1992; Gouda et al., 1998).

Figure 11B:
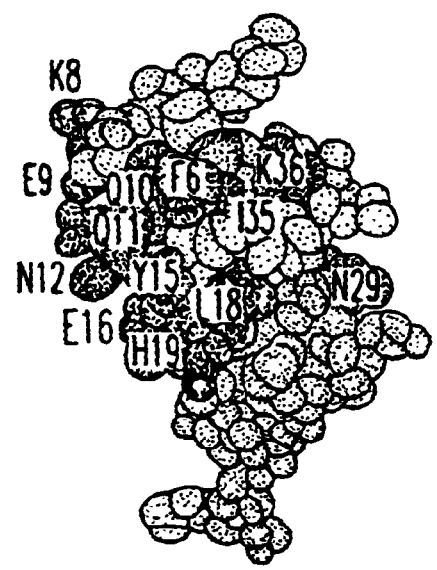
Figure 11C:
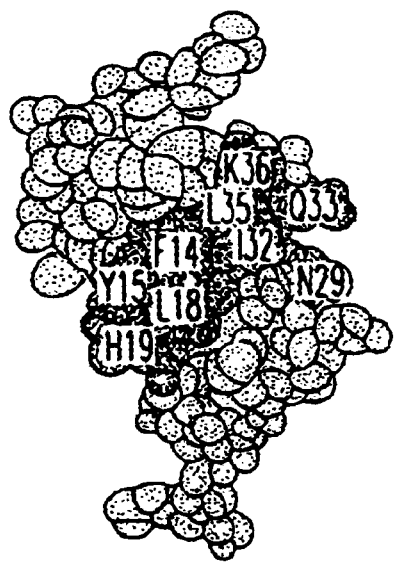

FIGS. 11(b) and (c) show the interaction sites revealed on the basis of the changes in the chemical shifts and the H-D exchange rates of the main chain amide protons of the FB molecule induced by binding the Fc fragment, respectively.

The NMR data (FIGS. 11(b) and (c)) indicate that helices I and II are primarily responsible for the binding of the FB molecule to the Fc fragment. However, it is found that the chemical shifts and the H-D exchange rates of some residues that were revealed to be on the contact surface by the X-ray crystallography study are hardly affected even upon Fc binding. Furthermore, the changes in the chemical shifts and the H-D exchange rates induced by binding the Fc fragment occur in residues from the surface of the FB molecule and also those from the interior thereof. Without being limited to any particular theory, the reason is thought to be because the binding of the Fc fragment affects the slight conformational change, the mobility, and the inside folding of the FB molecule, and indirectly affects the chemical shifts and the H-D exchange rates.

Figure 11D:
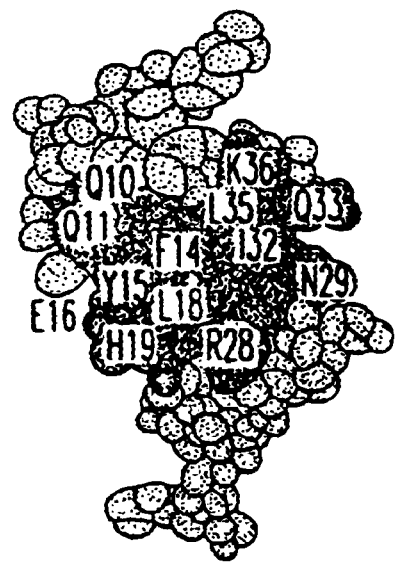

On the other hand, the residues revealed by the cross-saturation experiment to form the contact interface (FIG. 11(d)) are almost consistent with those revealed by the X-ray crystallography. Namely, the cross-saturation method can determine the contact interface more accurately as compared to the traditional method.

As described above, the inventive method is clearly superior to the traditional methods in which the changes in the chemical shifts and the H-D exchange rates are used as the indices (indicators). That is because, by using the present invention, following that, among the components of a biomolecular complex, nonexchangeable protons, preferably full nonexchangeable protons and at least 70% (no less than 70%) (preferably about (approximately) 80~90%) of exchangeable protons on a molecule with residues to be identified in the complex interface are exchanged, respectively to deuteriums, the residues on the contact surface of the complex can be determined more accurately through the cross-saturation phenomena. That can be achieved by the fact that the inventive method makes use of the cross-saturation phenomena strongly dependent on the space distance between two neighboring molecules, and furthermore the fact that, in this method, the partial deuteration can prevent the excess diffusion of the cross-saturation through the neighboring hydrogen atoms.

Because this method uses TROSY technique, the method of the present invention can readily be applied to other types of biomolecular complexes such as a protein-DNA or protein-lipid complexes as well as larger protein—protein complexes.

EXAMPLES

Having generally described this invention, a further understanding can be obtained by reference to certain specific examples which are provided herein for purposes of illustration only and are not intended to be limiting unless otherwise specified.

Example 1

Preparation of the FB Fragment

Genes (cf. Torigoe et al., 1990) coding a fusion protein which consists of the FB fragment of protein A and salmon growth hormone was amplified by PCR using two primers, SEQ ID No:1 and SEQ ID No:2.

(SEQ ID No:1)

5'-GCGCCC ATG GAAAACCAACGGCTCTTCAAC-3'

(SEQ ID No:2)

5'-GCGCGGATCC TTA GGCCTTTGGCGCCTGAG-3'

They are shown in the SEQ ID No: 1 and SEQ ID No: 2, respectively in the sequence listing (the underlines mean the restriction enzyme sites for BamHI and NcoI, respectively. The regions enclosed by frames mean the initiation codon and the termination codon, respectively). The PCR product was digested with two restriction enzymes, NcoI and BamHI, and was treated with T4 DNA ligase to be cloned into NcoI-BamHI site in pET3d vector DNA (Novagen, Inc., Madison, Wis.) (see FIG. 12 (Construction of *E. coli* expression system of the FB fragment of protein A, and the gene product are shown.)). *E. coli* BL21(DE3) cell (Novagen, Inc., Madison, Wis.) was transformed using the constructed expression vector, pET-SpA, and the base sequence of full length DNA of the ORF in the plasmid DNA of the ampicillin-resistant clone was confirmed (Pharmacia-Biotech Gene-Rapid DNA sequencer).

FB uniformly labeled with $^2$H and $^{15}$N was prepared by growing *E. coli* in M9 minimal media in 99.5% $^2$H$_2$O, using $^{15}$NH$_4$Cl and D-glucose-d$_7$ ([U-$^2$H]glucose) as the sole nitrogen and carbon sources, respectively, fundamentally according to the method as reported previously (cf. Venters et al., 1995). FB uniformly labeled with $^2$H, $^{13}$C, and $^{15}$N was prepared using [U-$^{13}$C]acetate as the sole carbon sources. 2 g of the *E. coli* cell were directly dissolved in 20 ml of 70% formic acid, followed by the addition of 1.0 g of BrCN with the final concentration of 50 mg/ml, and were stirred at room temperature for 2 hrs. At that time, the air of the reaction system was fully replaced with nitrogen gas. After the reaction, pH value was adjusted to 7.4 by addition of 50 ml of 20 mM PBS (pH7.4) and a proper amount of NaOH, followed by centrifugation at 25,000×g for 30 min. The supernatant obtained was applied to IgG Fast Flow column (φ1.5 cm×10 cm) (Pharmacia-Biotech) equilibrated with 2 mM PBS (pH 7.4). The sample was eluted from the column using 40 ml of 100 mM Gly-HCl (pH 3.0), and the full elution was fractionated and obtained. The fractions thus obtained were freeze-dried, dissolved in 15 ml of MilliQ water containing 0.1% TFA, and applied to ODS-AM AM-303 (YMC Co. Ltd.). The flow rate of the column chromatography was 1.0 ml/min with linear gradient of CH$_3$—CN (0–70%), and 20 ml of the elution was fractionated. The FB was eluted with around 30% (around) of the CH$_3$CN concentration. The low molecular weight impurities were removed by column chromatography using Superrose 12 column (φ12.0 cm×30 cm) (Pharmacia-Biotech) equilibrated with 20 mM PBS (pH 7.4), followed by the re-purification using reverse phase HPLC (high performance liquid chromatography). The proteins purified using the reverse phase HPLC were freeze-dried, followed by the determination of the quantity by measurement of the weight.

Preparation of the Fc Fragment

The Fc fragment was prepared by using IgG(κ) Ike-N originating from a human myeloma protein (cell), according to the method as reported previously (cf. Gouda et al., 1992).

Condition of NMR Measurements and Method of Data Analysis

The solution of the complex (64 kDa) between 1.0 mM FB (60 residues; 7 kDa) uniformly labeled with $^2$H and $^{15}$N and the unlabeled (nonlabeled) Fc fragment (50 kDa) mixed and dissolved in 450 μl of 20 mM PBS (pH 6.0) H$_2$O/D$_2$O was used for the sample in the experiments. The molar ratio of FB/Fc was 2/1.

NMR experiments (measurements) were carried out at 303 K as the measurement temperature on a Bruker DRX600 spectrometer.

Chemical shifts of proton were determined using the chemical shift of DSS as standard. Chemical shifts of $^{15}$N and $^{13}$C were determined indirectly on the basis of $^1$H/X absolute ratio of frequency for ammonia (0.10132905212) and DSS (0.2514495223), respectively (cf. Live et al., 1984; Bax and Subramanian, 1986; Wishart et al., 1995). All spectra were processed and analyzed with the program nmrPipe/nmrWish (cf. Delaglio et al., 1995).

TROSY-Cross Saturation Experiment

The cross-saturation experiments were performed using the pulse scheme shown in FIG. 4 (NMR pulse scheme for the cross-saturation method). 256×1024 data points were taken for the data matrices with acquisition times of 70.2 msec (t1) and 53.3 msec (t2).

Saturation of the aliphatic area protons of the Fc fragment was done using the WURST-2 decoupling scheme (cf. Kupce and Wagner, 1995). The maximum RF (radio frequency) amplitude (intensity) was 0.17 kHz for WURST-2 (the adiabatic factor Q$_0$=1). The saturation frequency was set at 0.9 p.p.m. The measurement times were 20 hrs with a recycle delay of 3.2 sec (2.0 sec for the adjusting delay (T$_{adj}$) and 1.2 sec for the saturation time (T$_{sat}$)).

TROSY-HNCA

For the 3D HNCA spectrum, 48×64×1024 data points were taken for the data matrix with acquisition times of 13.2 msec (t1), 7.1 msec (t2), and 61.1 msec (t3). The total measurement time was 2.0 days with the interscan delay (waiting period between each acquisition; relaxation delay) of 1.8 sec.

TROSY-HN(CO)CA

For the 3D HN(CO)CA spectrum, 48×64×1024 data points were taken for the data matrix with acquisition times of 13.2 msec (t1), 7.1 msec (t2), and 61.1 msec (t3). The total measurement time was 2.0 days with the interscan delay of 1.8 sec.

Estimation of T$_1$ Value of Amide Protons of the FB in Complex with a Fc Fragment It is expected that, compared with usual proteins, the longitudinal relaxation times of the FB amide protons will become much longer in the FB-Fc complex because the FB molecule is highly deuterated (cf. Wang et al., 1999). Therefore, to determine the optimum interpulse delay for the measurement of the cross-saturation, it is necessary to measure the longitudinal relaxation time of the amide protons. It can be estimated using ratios of signal intensities on water-flip-back TROSY-HSQC spectra that are measured with interpulse delays (including data acquisition times) of 2.5 sec and 5.0 sec. At that time, it is necessary to note that effects on the signals resulting from Boltzmann component (cf. Pervushin et al., 1998) of $^{15}$N must be removed by the two steps phase cycling (90$_{±y}$) in $^1$H just after the first INEPT.

FIG. 13 (Relaxation times of the FB uniformly labeled with 98% $^2$H/$^{15}$N in complex with the unlabeled (nonlabeled) Fc fragment) shows that T$_1$ of amide protons of the FB varies widely, and especially that the T$_1$ of some amide protons of helix III are longer than that of the others. The T$_1$ relaxation times of amide proton do not behave exponentially, but the observed (obtained) values correspond to the average value of recovery rate of magnetization occurring from 2.5 to 5.0 sec later since nuclear magnetizations of $^1$H are saturated. Considering the S/N ratio, it is proper for the FB-Fc complex to take about ~6 (around 6) sec for the interscan delay (waiting period between each measurements), but, in that case, the measurement time does not become reasonable even if the shortest measurement time to obtain and observe a HSQC spectrum with a required resolution ability is chosen. As the compromise between the S/N ratio and the resolution, the interscan delay (corresponding to T$_{adj}$+T$_{sat}$ for the cross-saturation) of 3.2 sec was used for the practical measurements (experiments).

Band of Radio Frequency (Stretched Adiabatic Pulse WURST2) for the Cross-Saturation It has been already confirmed by the $^1$H-1D NMR spectrum that the saturation of the Fc fragment is achieved sufficiently, but, here, the range of frequency in which the radio frequency used here can act effectively was obtained and studied more minutely using a saturation of a single proton signal. FIG. 14 (The band of radio frequency for the cross-saturation) is the result of the NMR spectrum in which the band of the WURST-2 type adiabatic shaped-pulse used for the cross-saturation is revealed through surveys and observation of saturation of DSS methylene protons (1.755 p.p.m.). The spectrum shows that the region of about (nearly) 2.0 kHz is saturated effectively. The region corresponds to that indicated in FIG. 5 (Confirmation of saturation of the Fc fragment by the $^1$H-1D NMR spectrum) (a), and it is suggested that methyl protons of the Fc fragment can be saturated selectively, and that the region of water signal is hardly affected.

Assignment of NMR Signals of the FB

The assignment of $^1$H-$^{15}$N HSQC NMR signals arising from the protein backbone amide group (nuclei) of the FB was made using the sequential resonance assignment method. Table 1 (Protein backbone amide nitrogen and amide proton chemical shifts for the FB) shows the chemical shifts of the NMR signals of protein backbone amide nitrogens and amide protons for each amino acid residue of the FB.

TABLE 1

| Residue No. | Amino acid type | free FB $^1$H$_N$ | free FB $^{15}$N$_H$ | Fc-bound FB $^1$H$_N$ | Fc-bound FB $^{15}$N$_H$ |
|---|---|---|---|---|---|
| 1 | THR | | | | |
| 2 | ALA | 8.301 | 127.143 | 8.318 | 126.971 |
| 3 | ASP | 8.184 | 121.008 | 8.260 | 121.168 |
| 4 | ASN | 8.112 | 120.301 | 8.348 | 119.595 |
| 5 | LYS | 8.072 | 122.232 | 8.005 | 122.602 |
| 6 | PHE | 7.969 | 121.057 | 7.539 | 119.687 |
| 7 | ASN | 8.326 | 122.005 | 8.179 | 122.821 |
| 8 | LYS | 8.213 | 120.443 | 8.826 | 131.924 |
| 9 | GLU | 8.149 | 121.012 | 8.396 | 122.934 |
| 10 | GLN | 8.397 | 122.575 | 8.165 | 123.158 |
| 11 | GLN | 8.565 | 120.276 | 7.758 | 121.002 |
| 12 | ASN | 8.192 | 119.301 | 8.378 | 119.815 |
| 13 | ALA | 7.831 | 123.850 | 8.088 | 122.216 |
| 14 | PHE | 8.044 | 119.149 | 8.037 | 118.846 |
| 15 | TYR | 8.031 | 118.374 | 7.993 | 120.088 |
| 16 | GLU | 8.473 | 120.627 | 8.537 | 117.349 |
| 17 | ILE | 8.328 | 120.866 | 8.391 | 121.185 |
| 18 | LEU | 7.810 | 118.878 | 8.097 | 121.369 |
| 19 | HIS | 7.152 | 113.152 | 6.666 | 111.691 |
| 20 | LEU | 7.106 | 125.623 | 7.097 | 125.593 |
| 22 | ASN | 8.794 | 115.193 | 8.803 | 115.167 |
| 23 | LEU | 6.426 | 118.488 | 6.448 | 118.407 |
| 24 | ASN | 8.448 | 120.445 | 8.348 | 119.595 |
| 25 | GLU | 8.489 | 119.672 | 8.432 | 120.285 |
| 26 | GLU | 8.142 | 121.189 | 8.378 | 119.815 |
| 27 | GLN | 8.486 | 121.156 | 8.541 | 121.094 |
| 28 | ARG | 8.540 | 120.927 | 8.629 | 121.448 |
| 29 | ASN | 8.513 | 116.923 | 8.819 | 117.985 |
| 30 | GLY | 7.921 | 109.635 | 8.081 | 110.911 |
| 31 | PHE | 7.695 | 121.671 | 7.843 | 121.520 |
| 32 | ILE | 8.141 | 119.827 | 8.198 | 119.250 |
| 33 | GLN | 8.312 | 120.376 | 8.303 | 120.810 |
| 34 | SER | 7.884 | 116.349 | 7.940 | 116.655 |
| 35 | LEU | 8.047 | 125.547 | 7.960 | 122.484 |
| 36 | LYS | 7.876 | 117.060 | 7.633 | 120.597 |
| 37 | ASP | 7.980 | 119.231 | 7.952 | 119.780 |
| 38 | ASP | 7.507 | 115.238 | 7.585 | 115.293 |
| 40 | SER | 7.952 | 114.375 | 8.236 | 116.618 |
| 41 | GLN | 7.770 | 121.617 | 7.710 | 121.546 |
| 42 | SER | 7.661 | 116.744 | 7.430 | 116.787 |
| 43 | ALA | 8.368 | 124.129 | 8.493 | 123.172 |
| 44 | ASN | 7.801 | 119.677 | 7.911 | 120.113 |
| 45 | LEU | 8.480 | 122.796 | 8.632 | 123.364 |
| 46 | LEU | 8.290 | 120.040 | 8.160 | 120.147 |
| 47 | ALA | 7.476 | 120.696 | 7.555 | 120.804 |
| 48 | GLU | 7.930 | 120.665 | 8.022 | 120.657 |
| 49 | ALA | 8.300 | 125.012 | 8.326 | 125.237 |
| 50 | LYS | 8.379 | 119.311 | 8.416 | 119.428 |
| 51 | LYS | 7.600 | 121.400 | 7.594 | 121.262 |
| 52 | LEU | 7.816 | 123.354 | 7.859 | 123.582 |
| 53 | ASN | 8.457 | 118.238 | 8.510 | 118.217 |
| 54 | ASP | 8.149 | 120.055 | 8.116 | 120.062 |
| 55 | ALA | 7.917 | 124.092 | 7.945 | 124.170 |
| 56 | GLN | 7.441 | 116.261 | 7.475 | 116.268 |
| 57 | ALA | 7.035 | 125.683 | 7.067 | 125.694 |
| 59 | LYS | 8.330 | 123.914 | 8.342 | 123.916 |
| 60 | ALA | 7.846 | 132.145 | 7.854 | 132.162 |

Simulation of the Cross-Saturation

The principle of the cross-saturation phenomena is a cross-relaxation arising from spin—spin interactions among magnetizations of proton nuclei. Because the cross-relaxation depends on the distance between spins, the behavior of cross-relaxation can be estimated using the distance between proton spins. Here, a simulation of the cross-saturation was made using the coordinates of the FB-Fc complex obtained from the X-ray crystal structure (crystallography study). In the simulation, when protons in the Fc fragment were saturated for 1.5 sec, the extent of cross-saturation which, was received by the proton magnetizations of the FB was estimated. The simulation of the cross-saturation was accomplished with the modified CORONA program (cf. Zheng et al., 1997).

In FIG. 15 (simulation of the cross-saturation), signal changes of amide protons in the amino acid residues located around helix I of the FB are plotted. The water/deuterium oxide ratio (concentration) in the solvent used here are 0% $H_2O$/100% $^2H_2O$, 10% $H_2O$/90% $^2H_2O$ and 90% $H_2O$/10% $^2H_2O$. In the mean time, when the water/deuterium oxide ratio in the solvent is 0% $H_2O$/100% $^2H_2O$, the observable protons are only the protons of the FB molecule, and the situation corresponds to the result obtained in the condition with no interaction among protons in the molecule. Compared with the case of 0% $H_2O$/100% $^2H_2O$, the result of 10% $H_2O$/90% $^2H_2O$ is almost the same in the results obtained. On the other hand, in the case of 90% $H_2O$/10% $^2H_2O$, changes of signal intensity of the two adjacent amide protons show almost the same extent. The reason is thought that the intramolecular spin diffusions have occurred effectively because distances among amide protons are narrow (shorter) in the condition of the 90% $H_2O$/10% $^2H_2O$. On the other side, because the result obtained in the condition of the 10% $H_2O$/90% $^2H_2O$ is almost the same as the result in the condition of the 0% $H_2O$/100% $^2H_2O$ in which adjacent protons in the FB molecule are fully independent with each other, it is thought that the distances among amide protons in the FB molecule and other protons in the molecule are so long in the condition of the 10% $H_2O$/90% $^2H_2O$ as the interactions among spins can be ignored, and that the effects of spin diffusion in the FB molecule in the complex are suppressed to the extent to be ignored.

Saturation Time($T_{sat}$) in the Cross-Saturation

It is the point for the cross-saturation to observe it in the condition that the intramolecular relaxations are suppressed, but the stronger intramolecular relaxations can also be observed by extension of the saturation time. Namely, the saturation time ($T_{sat}$) is one of the important factors for the cross-saturation, and it is important to use the longest saturation time within the limits for the suppression of the intramolecular relaxations. FIG. 16 (changes in signal intensity with the saturation time ($T_{sat}$)) shows the effect of the saturation time on the signal intensity ratios of the crosspeaks originating from the backbone amide groups with irradiation of radio frequency to those without irradiation of radio frequency. The figure shows that, with the saturation time ($T_{sat}$=1.2 sec) used for the cross-saturation, the spin diffusions in the FB molecule even in the large (molecular weight) complex (Mw: 64,000) are not generated, and, at the same time, the efficient reductions of signal intensity of the crosspeaks can be observed. It should be noted that the concentration of $H_2O$ in the sample solvent used for this method is considerably low.

Effect of $H_2O$ Concentration in Solvent on the Cross-Saturation

For the cross-saturation (the saturation transfer from the Fc fragment to the FB molecule), a condition in which the proton density in the FB molecule was kept low with the proton concentration of the solvent of 10% in order to observe the cross-saturation phenomena only on the contact interface of the complex was taken. Actually, in the condition of 90% $H_2O$, the intramolecular relaxations occurred strongly, and almost the same reductions of the NMR signal intensities were observed in helices where the distances among protons were very short. By the way, because the reduction of the $H_2O$ (light water) concentration of the solvent is equal to the reduction of the concentration of NMR observable nucleus, the method has a weak point that the measurement time of NMR spectrum becomes longer.

Therefore, in practice, it is important to find the highest $H_2O$ (water, light water) concentration of the solvent in which the intramolecular relaxation does not occur. Same as the above simulation of the cross-saturation, simulations in different $H_2O$ concentrations of the solvent have been done, and the results are shown in FIG. 17 (Effects of $H_2O$ concentration in the solvent on the cross-saturation). Compared with results obtained with 10% $H_2O$/90% $^2H_2O$ ((a) dotted line), it is found that the changes in signal intensity obtained with in the condition of 20% $H_2O$/80% $^2H_2O$ ((a) solid line) were almost the same. On the other hand, with 30% $H_2O$/70% $^2H_2O$ ((b) solid line), the differences of the signal intensity changes between the adjacent amino acid residues became smaller. That is because the proton density in the molecule became so high that the intramolecular relaxation phenomena could not be ignored. This condition is thought not to be suitable for the cross-saturation. On the basis of the above results, it is concluded that the cross-saturation phenomenon in the solvent of 20% $H_2O$/80% $^2H_2O$ is the best condition. In practice, a measurement was done in that condition, and almost the same result as obtained in 10% $H_2O$/90% $^2H_2O$ was obtained. The result of the cross-saturation (20% $H_2O$/80% $^2H_2O$) and the plots of the signal intensity ratios of the crosspeaks in the cross-saturation experiments (20% $H_2O$/80% $^2H_2O$) are shown in FIGS. 18 and 19, respectively.

Obviously, numerous modifications and variations of the present invention are possible in light of the above teachings. It is therefore to be understood that within the scope of the appended claims, the invention may be practiced otherwise than as specifically described herein.

This application is based on the Japanese Patent Application Serial No. 2000-214997, filed on Jul. 14, 2000, and article Takahashi et. al., "A novel NMR method for determining the interfaces of large protein—protein complexes", Nature Structural Biology, vol. 7, No. 3, March 2000, pp. 220–223, each of which are incorporated herein by reference.

REFERENCES

1. Akasaka, K. (1981), Longitudinal relaxation of protons under cross saturation and spin diffusion. J. Magn. Res. 45, 337–343.
2. Bax, A. and Subramanian, S. (1986), Sensitivity-Enhanced Two-Dimensional Heteronuclear Shift Correlation NMR Spectroscopy. J. Magn. Reson. 67, 565–569.
3. Clackson, T., Wells, J. A. (1995), A Hot Spot of Binding Energy in a Hormone-Receptor Interface. Science 267, 383–386.
4. Cunningham, B. C. and Wells, J. A. (1997), Minimized proteins. Curr. Opin. Struct. Biol. 7, 457462.
5. Deisenhofer, J. (1981), Crystallographic refinement and atomic models of a human Fc fragment and its complex with fragment B of protein A from Staphylococcus aureus at 2.9- and 2.8-Å resolution. Biochemistry. 20, 2361–2370.
6. Delaglio, F., Grzesiek, S., Vuister, G., Zhu, G., Pfeifer, J. and Bax, A. (1995), NMRpipe: a multidimentional spectral processing system based on UNIX pipes. J. Biomol. NMR 6, 277–293.
7. Foster, M. P., Wuttke, D. S., Clemens, K.R., Jahnke, W., Radhakrisbnan, I., Tennant, L., Reymond, M., Chung, J. and Wright, P. E. (1998), Chemical shift as a probe of molecular interface: NMR studies of DNA binding by the three amino-terminal zinc finger domains from transcription factor IIIA. J. Biomol. NMR 12, 51–71.
8. Gouda, H., Torigoe, H., Saito, A., Sato, M., Arata, Y. and Shimada, I. (1992), Three-dimentional solution structure of the B domain of staphylococcal protein A: comparisons of the solution and crystal structures. Biochemistry. 31, 9665–9672.
9. Gouda, H., Shiraishi, M., Takahashi, H., Kato, K., Torigoe, H., Arata, Y. and Shimada, I. (1998), NMR study of the interaction between the B domain of staphylococcal protein A and the Fe portion of immunoglobulin G. Biochemistry. 37, 129–136.
10. Jedenberg, L., Tashiro, M., Tejero, R., Lynos, B. A., Uhlén, M., Montelione, G. T., Nilsson, B. (1996), The mechanism of binding staphylococcal protein A to immunogloblin G dose not involve helix unwinding. Biochemistry 35, 22–31.
11. Kalk, A. and Berendsen, H. J. C. (1976), Proton magnetic relaxation and spin diffusion in proteins. J. Magn. Res., 24, 343–366.
12. Kupce. and Wagner, G. (1995), Wideband homonuclear decoupling in proteinspectra. J. Magn. Res. B. 109, 329–333.
13. Langone, J. J. (1982), Protein A of Staphylococcus aureus and related immunoglobulin receptors produced by streptococci and pneumonococci. Adv. Immunol. 32, 157–252.
14. Live, D. H., Davis, D. G., Agosta, W. C. and Cowburn, D. (1984), Long Range Hydrogen Bond Mediated Effects in Peptides: 15N NMR Study of Oramicidin S in Water and Organic Solvents. J. Am. Chem. Soc. 106, 1939–1943.
15. Paterson, Y., Englander, S. W. and Roder, H. (1990), An antibody binding site on cytochrome c defined by hydrogen exchange and two-dimensional NMR. Science. 249, 755–759.
16. Pervushin, K., Riek, R., Wider, O. and Wuetrich, K. (1998), Attenuated T2 relaxation by mutual cancellation of dipole—dipole coupling and chemical shift anisotropy indicates an avenue to NMR structure of very large biological macromolecules in solution. Proc. Nat. Acad. Sci. USA. 94, 12366–12371.

17. Pervushin, K., Wider, O. and Wuetrieh, K. (1998), Single transition-to-single transition polarization transfer (ST2-PT) in [15N, 1H]-TROSY. J. Biomol. NMR 12, 345–348.
18. Salzmann, M., Pervushin, K., Wider, G., Senn, H. and Wuetbrich, K. (1998), TROSY in triple-resonance experiments: new perspectives for sequential NMR assignment of large proteins. Proc. Natl. Acad. Sci. USA. 95, 13585–13590.
19. Salzmann, M., Wider, O., Pervushin, K., Semi, H. and Wuethrich, K. (1999), TROSY in Triple-Resonance Experiments For Sequential NMR Assignments of Large Proteins. J. Am. Chem. Soc. 121, 844–848.
20. Song, J. and Ni, F. (1998), NMR for the design of functional mimetics of protein—protein interactions: one key is in the building of bridges. Biochem. Cell Bid. 76, 177–188.
21. Torigoe H., Shimada, I., Saito, A., Sato, M. and Arata, Y. (1990), Sequential 1H NMR assignments and secondary structure of the B domain of staphylococcal protein A: structural changes between the free B domain in solution and the Fc-bound B domain in crystal. Biochemistry. 29, 8787–8793.
22. Venters, R. A., Huang C. C., Farmer II, B. T., Troland, R., Spicer, L. D. and Fierke, C.A. (1995), High-level 2H/13C/15N labeling of proteins for NMR studies. J. Biomol. NMR 5, 339–344.
23. Wang, Y. X., Jacob, J., Cordier, F., Wingfield, P. T., Palmer, I., Stahl, S. J., Lee-Huang, S., Torchia, D. A., Grzesiek, S., and Bax, A. (1999). Measurement of (3 h)J(NC') connectivities across hydrogen bonds in a 30 kDa protein. J. Biomol. NMR 14, 181–184.
24. Wells, J. A. (1991), Systematic mutational analysis of protein—protein interfaces. Methods Enzymol. 202, 390–411.
25. Wishart, D. S., Bigam, C. G., Yao, J., Abildgaard, F., Dyson, H.J., Oldfteld, E., Markley, J. and Sykes, B. D. (1995), 1H, 13C and 15N Chemical shift Referencing in Biomolecular NMR. J. Biomol. NMR 6, 135–140.
26. Zheng, J., Zabell, A. P. R., Post C. B., (1997), CORONA: A Program to Analyze and Simulate NOESY Intensities by Matrix Methods for Multiple Spin Pair Interactions. Purdue University, West Lafayette.
27. de Vos, A. M., Ultsch, M., Kossiakoff, A. A. (1992), Human Growth Hormone and Extracellular Domain of Its Receptor: Crystal Structure of the Complex. Science 255, 306–312.

What is claimed is:
1. A method for identifying an interface residue in a biomolecular complex comprising at least two biomolecules, comprising:
   substituting at least a majority of nonexchangeable hydrogens and at least 70% of the exchangeable hydrogens in a first biomolecule to deuterium;
   labeling the first biomolecule with at least one heavy atom;
   irradiating at least a portion of the protons of a second biomolecule in the biomolecular complex at their NMR frequency; and
   identifying the position of an exchangeable hydrogen which is located on said one biomolecule in the complex which is within 10 angstrom from a hydrogen present in the other biomolecule and receives a cross-saturation by a cross-saturation phenomena.
2. The method of claim 1, wherein the complex consists of two biomolecules.
3. The method of claim 1, wherein from 80 to 90% of the exchangeable hydrogens are exchanged to deuterium.
4. The method of claim 1, wherein the cross-saturation phenomena are induced by an adiabatic shaped-pulse method.

5. The method of claim 1, wherein the biomolecules are each, independently, a protein, a nucleic acid, or a lipid.

6. The method of claim 1, wherein at least one of the biomolecules is a protein.

7. The method of claim 1 or claim 2, wherein at least one of the biomolecules is a protein, a nucleic acid, or a lipid.

8. The method of claim 1, wherein at least 80% of the nonexchangeable hydrogens are exchanged to deuterium.

9. The method of claim 1, wherein all of the nonexchangeable hydrogens are exchanged to deuterium.

10. The method of claim 1 or 2, wherein the biomolecular complex is prepared by exchanging a majority of the non-exchangeable hydrogens and at least 70% of the exchangeable hydrogens of one biomolecule to deuterium and then combined with other molecule(s) to produce the biomolecular complex.

11. The method of claim 1, wherein at least a portion of the nitrogen atoms in said one biomolecule are $^{15}N$.

12. The method of claim 1, wherein the identifying is performed by observing a $^1H$-$^{15}N$ TROSY-HSQC spectra.

13. The method of claim 12, wherein the identifying is performed by comparing the $^1H$-$^{15}N$ TROSY-HSQC spectra of the labeled complex with that of a complex not labeled.

14. The method of claim 4, wherein the adiabatic shaped-pulse is of the WURST-2 type.

* * * * *

SEQUENCE LISTING

```
<160> NUMBER OF SEQ ID NOS:  2

<210> SEQ ID NO 1
<211> LENGTH: 30
<212> TYPE: DNA
<213> ORGANISM: Artificial
<220> FEATURE:
<223> OTHER INFORMATION: synthetic primer

<400> SEQUENCE: 1
gcgcccatgg aaaaccaacg gctcttcaac                                    30

<210> SEQ ID NO 2
<211> LENGTH: 30
<212> TYPE: DNA
<213> ORGANISM: Artificial
<220> FEATURE:
<223> OTHER INFORMATION: synthetic primer

<400> SEQUENCE: 2
gcgcggatcc ttaggccttt ggcgcctgag                                    30
```